US012778467B2

(12) United States Patent
Jornet et al.

(10) Patent No.: US 12,778,467 B2
(45) Date of Patent: Nov. 3, 2026

(54) IMPLANTABLE BIOSENSOR AND COMMUNICATION NODE WITH PLASMONIC NANO-ANTENNA

(71) Applicant: Northeastern University, Boston, MA (US)

(72) Inventors: Josep Miquel Jornet, Needham, MA (US); Amit Sangwan, Boston, MA (US)

(73) Assignee: Northeastern University, Boston, MA (US)

( * ) Notice: Subject to any disclaimer, the term of this patent is extended or adjusted under 35 U.S.C. 154(b) by 291 days.

(21) Appl. No.: 18/685,454

(22) PCT Filed: Aug. 26, 2022

(86) PCT No.: PCT/US2022/041765
§ 371 (c)(1),
(2) Date: Feb. 21, 2024

(87) PCT Pub. No.: WO2023/028355
PCT Pub. Date: Mar. 2, 2023

(65) Prior Publication Data
US 2024/0350045 A1 Oct. 24, 2024

Related U.S. Application Data

(60) Provisional application No. 63/237,874, filed on Aug. 27, 2021.

(51) Int. Cl.
*A61B 5/1459* (2006.01)
*A61B 5/00* (2006.01)

(52) U.S. Cl.
CPC .......... *A61B 5/1459* (2013.01); *A61B 5/0017* (2013.01)

(58) Field of Classification Search
CPC ... A61B 5/1459; A61B 5/0017; A61B 5/0031; A61B 5/686; A61B 5/6861; G01N 21/554; G01N 21/7703
See application file for complete search history.

(56) References Cited

U.S. PATENT DOCUMENTS

2015/0247797 A1* 9/2015 Oberg .................. A61B 5/1451 600/302
2016/0069810 A1* 3/2016 Walavalkar ............ G01N 33/18 356/301

(Continued)

OTHER PUBLICATIONS

Akyildiz, et al., "Electromagnetic wireless nanosensor networks," Nano Communication Networks, Broadband Wireless Networking Laboratory, School of Electrical and Computer Engineering, Georgia Institute of Technology, Atlanta, GA, US, (2010).

(Continued)

*Primary Examiner* — Eric J Messersmith
(74) *Attorney, Agent, or Firm* — Hamilton, Brook, Smith & Reynolds, P.C.

(57) ABSTRACT

A biosensor that is configured to be implanted into a living being includes a light source configured to generate source light with a source light spectrum. The biosensor also includes plasmonic nano-antenna optically coupled to the light source to receive the source light and to emit light therefrom exhibiting a spectral signature of the plasmonic nano¬antenna. A bio-functionalized element joined to the plasmonic nano-antenna can receive a biomarker if available and effect a change in the spectral signature as a function of receipt or nonreceipt of the biomarker. A combination of the light source and nano-antenna can encode an optical communication signal into the emitted light and transmit the signal to a separate communication node. An optional detector can detect the emitted light and provide output indicative of receipt or nonreceipt of the biomarker, which can in turn (Continued)

be encoded into the communication signal for reporting to another node.

20 Claims, 11 Drawing Sheets

(56) References Cited

U.S. PATENT DOCUMENTS

| | | | | |
|---|---|---|---|---|
| 2017/0238804 | A1* | 8/2017 | Hartley | G02B 1/005 |
| 2021/0121065 | A1* | 4/2021 | Jornet | A61B 5/0004 |

OTHER PUBLICATIONS

Maksymov, "Magneto-plasmonic nanoantennas: Basics and applications," Reviews in Physics, 1:36-51 (2016).
Sangwan, "Joint Communication and Bio-sensing with Plasmonic Nano-Systems to Prevent the Spread of Infectious Diseases in the Internet of Nano-Bio Things," Journal on Selected Areas in Communications, vol. XX, No. X, Jan. 2022.
Eisa Zarepour, et al., "Semon: Sensorless event monitoring in self-powered wireless nanosensor networks," The University of New South Wales, Technical Report UNSW-CSE-TR-201602 (Feb. 2016).
Sangwan, Amit, et al., "Beamforming optical antenna arrays for nano-bio sensing and actuation applications", Nano Communication Networks, Elsevier, Amsterdam, NL, vol. 29, XP086724778, ISSN: 1878-7789 (2021).
Guo, Hongzhi, et al., "Cooperative Raman 17 Spectroscopy for. Real-time In Vivo Nano-biosensing", arxiv.org, Cornell University Library, 201 Olin Library Cornell University Ithaca, NY 14853, Mar. 27, 2017.
Somin, Eunice Lee, et al, "Biomolecular 1-6,12, plasmonics for quantitative biology and 13, nanomedicine", 17-22, Current Opinion in Biotechnology, vol. 21, No. 4, pp. 489-497 (2010).
Guo, Hongzhi, et al., "Intra-Body Optical 1-6,12, Channel Modeling for In Vivo Wireless 13,Nanosensor Networks", 17-22, IEEE Transactions on Nanobioscience, IEEE 24-26,28 Service Center, Piscataway, NY, US, vol. 15, No. 1, pp. 41-52 (2016).
International Search Report and Written Opinion for International Application No. PCT/US2022/041765, entitled "Implantable Biosensor and Communication Node With Plasmonic Nano-Antenna," 22 pages, mailing date Jan. 13, 2023.

* cited by examiner

IMPLANTABLE BIOSENSOR AND COMMUNICATION NODE WITH PLASMONIC NANO-ANTENNA

RELATED APPLICATION(S)

This application is the U.S. National Stage of International Application No. PCT/US2022/041765, filed Aug. 26, 2022, which designates the U.S., published in English, and claims priority under 35 U.S.C. § 119 or 365 to U.S. Provisional, Application No. 63/237,874, filed Aug. 27, 2021. The entire teachings of the above application(s) are incorporated herein by reference.

GOVERNMENT SUPPORT

This invention was made with government support under 2039189 from the National Science Foundation. The government has certain rights in the invention.

BACKGROUND

Nanotechnology has advanced and played a pivotal role in today's society. Plasmonic sensing has demonstrated unprecedented detection reliability and resolution in a compact form factor. Traditional plasmonic sensors leverage bio-functionalized metallic grating structures whose frequency response in transmission or reflection changes according to a presence of targeted biomarkers.

SUMMARY

Existing biosensing setups require bulky measurement equipment to couple light to and from sensors for excitation and detection. In parallel with the development of plasmonic nano-sensing, the nanoscale electromagnetic communication community has been using plasmonic structures to transmit information at the nanoscale efficiently.

The inventors have recognized that these two realms of sensing and communication may be co-implemented in embodiments in a manner to produce advantages over either one alone and to enable nanoscale biosensing with simultaneous communication in order to enable both technologies to the implanted within a living being within the same biosensor. Disclosed herein are embodiments that take implement joint nanoscale communication and biosensing enabled by biosensing nano-antennas. Sensing nano-nodes can communicate from nano-node to nano-node for intra-body networks and from nano-node to a wearable device. In addition, edge computing and networking can be leveraged in order to process and transmit the sensing information to the cloud. This has the further advantage of enabling accurate diagnosis and reducing load on the medical testing infrastructure.

Disclosed herein is a modeling of the changes in frequency response of a bio-functionalized plasmonic nano-antenna when exposed to different biomarkers. Further disclosed herein is a chirp-spread spectrum excitation and detection method that can be implemented in the embodiments as one way of enabling simultaneous communication and sensing at the nanoscale. A data-driven human tissue model of communication through human tissue is included. Numerical results to demonstrate superior performance of embodiments are also disclosed.

In one particular embodiment, a biosensor includes:

a) a light source at a biosensor, the light source configured to generate source light having a source light spectrum, and the biosensor configured to be implanted into a living being;

b) a plasmonic nano-antenna at the biosensor, the plasmonic nano-antenna optically coupled to the light source and configured to receive the source light and to emit light therefrom exhibiting a spectral signature of the plasmonic nano-antenna; and c) a bio-functionalized element joined to the plasmonic nano-antenna and configured to receive a biomarker if the biomarker is available, the bio-functionalized element configured to effect a change in the spectral signature as a function of receipt or nonreceipt of the biomarker, d) wherein a combination of the light source and the plasmonic nano-antenna is configured to encode an optical communication signal into the emitted light exhibiting the spectral signature, and e) wherein the combination is further configured to transmit the optical communication signal, via the emitted light exhibiting the spectral signature, to a communication node that is physically separated from the biosensor.

Among other optional features, the biosensor can further optionally and advantageously include a detector at the biosensor, the detector configured to detect the emitted light and to provide an output indicative of the receipt or nonreceipt of the biomarker by the bio-functionalized element. The combination of the light source and the plasmonic nano-antenna optionally and advantageously can be further configured to encode the output indicative of the receipt or nonreceipt of the biomarker into the optical communication signal.

The light source, the plasmonic nano-antenna, and the detector optionally and advantageously mounted onto a common chip.

In another embodiment, a communication node includes a) a light source at a first communication node, the light source configured to generate source light having a source light spectrum, and the first communication node configured to be implanted into a living being; and b) a plasmonic nano-antenna at the first communication node, the plasmonic nano-antenna optically coupled to the light source and configured to receive the source light and to emit light exhibiting a spectral signature of the plasmonic nano-antenna, c) wherein the first communication node is configured to send an optical communication signal to a second communication node that is physically separated from the first communication node by using the emitted light exhibiting the spectral signature of the plasmonic nano-antenna.

The communication node can further include a bio-functionalized element joined to the plasmonic nano-antenna and configured to receive a biomarker if the biomarker is available, the bio-functionalized element configured to effect a change in the spectral signature as a function of receipt or nonreceipt of the biomarker.

The communication node can further include a detector configured to detect the emitted light exhibiting the spectral signature and provide an output indicative of whether the biomarker is received based on the spectral signature.

The communication node can further include a modulator configured to modulate the source light with a modulation as a function of the output indicative of whether the biomarker is received, the modulation causing the output indicative of whether the biomarker is received to be encoded into the communication signal.

Figure 1:
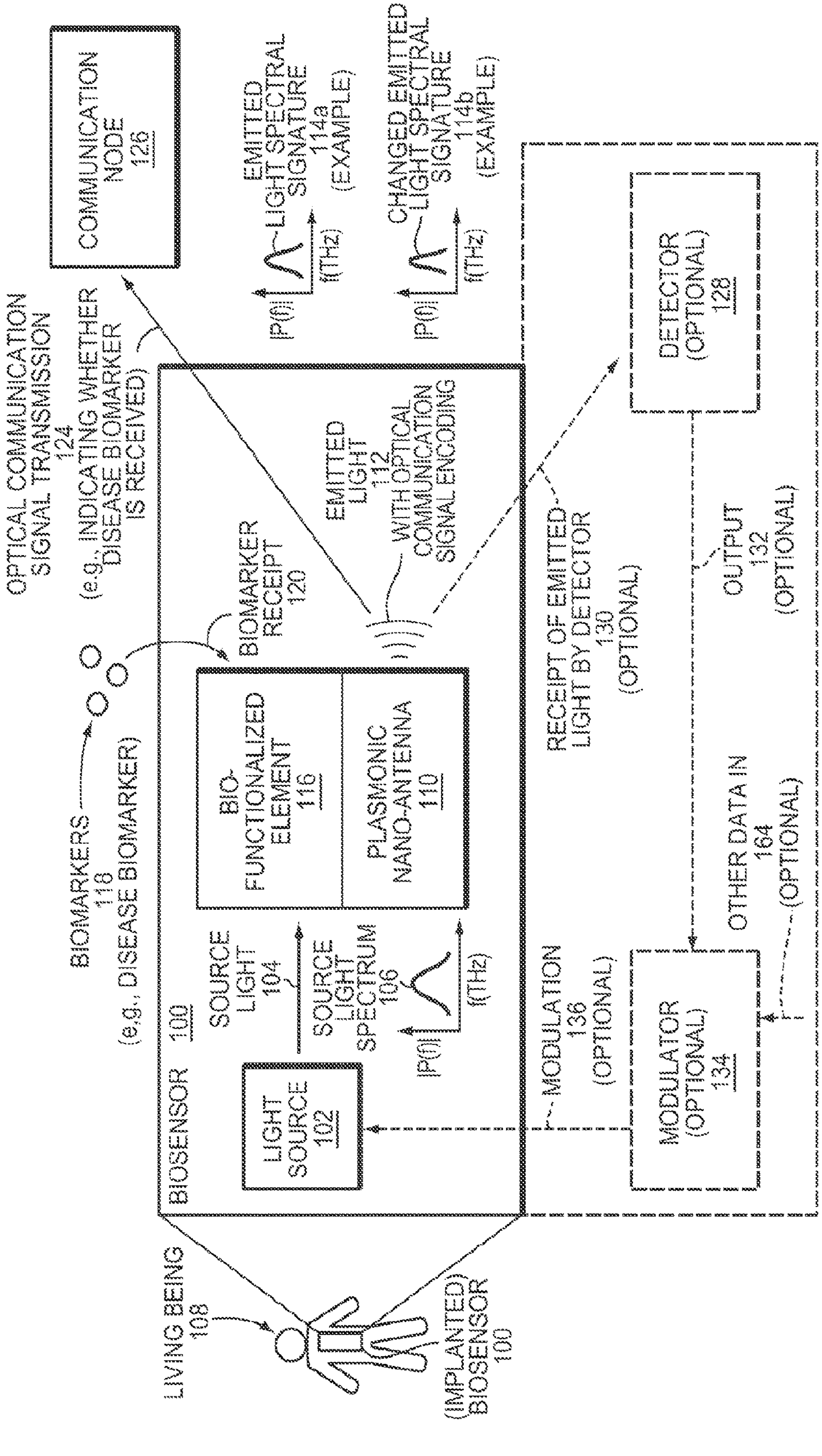
FIG. 1 is a schematic block diagram illustrating an embodiment biosensor with a plasmonic nano-antenna that is configured both to sense presence of a biomarker and to send a communication to a physically separate communication node using the same light emitted from the plasmonic nano-antenna.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

FIG. 1 is a schematic block diagram illustrating an embodiment biosensor 100 including a light source 102, plasmonic nano-antenna 110, and bio-functionalized element 116, along with an optional detector 128 and optional modulator 134.

The light source and plasmon nano-antenna are "at" the biosensor 100, indicating that they are part of the same implantable biosensor forming one biosensor unit. In one example, the light source 102 and plasmonic nano-antenna 110 can be encompassed by, or held within, a biocompatible housing of the biosensor, as illustrated in example FIG. 22. In another example, the light source 102 and plasmonic nano-antenna 110 are "at" the biosensor 100 because they are situated on a common chip that forms part of the biosensor 100, as illustrated in example FIG. 4.

The biosensor 100 is configured to be implanted in a living being 108, as illustrated at the left of FIG. 1, and as further illustrated in FIGS. 3, 10A, 11A, and 12A.

Figure 15A:
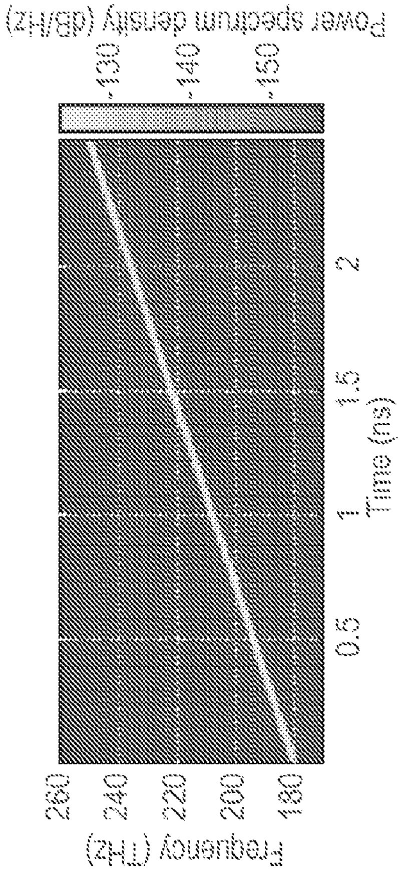
FIG. 15A is a graph showing a power spectrum of an example linear chirp signal that can be used for antenna excitation in a chirp light source in embodiments.
Figure 16:
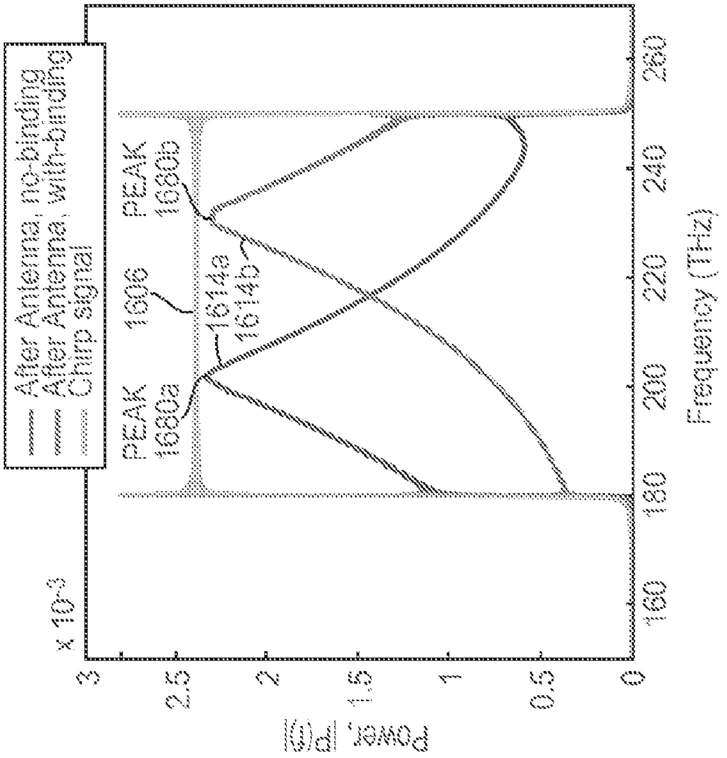
FIG. 16 is a graph illustrating chirp source light signal power versus the plasmonic antenna response for non-binding and binding cases.

The light source 102 is configured to generate source light 104 that has a source light spectrum, such as the example source light spectrum 106 illustrated in FIG. 1. The source light spectrum, as shown, may be represented as power spectral density, or absolute value of power spectral density, as a function of frequency. However, the source light spectrum 106 can be represented in other ways, and via other units, as illustrated in FIGS. 15A and 16, for example.

The plasmonic nano-antenna 110 is optically coupled to the light source 102 in a manner such that the plasmonic nano-antenna 110 is configured to receive the source light 104. The plasmonic nano-antenna 110 is further configured to emit light 112 therefrom, with the emitted light 112 exhibiting a spectral signature of the plasmonic nano-antenna. A bio-functionalized element 116 is joined to the plasmonic nano-antenna and configured to receive a biomarker 118 (e.g., a disease biomarker) if the biomarker is or becomes available (sufficiently proximal to) the bio-functionalized element 116. Bio-functionalized elements are described further hereinafter, by way of example, in connection with FIG. 2, FIG. 4, FIG. 5, and FIG. 6.

Figure 21:
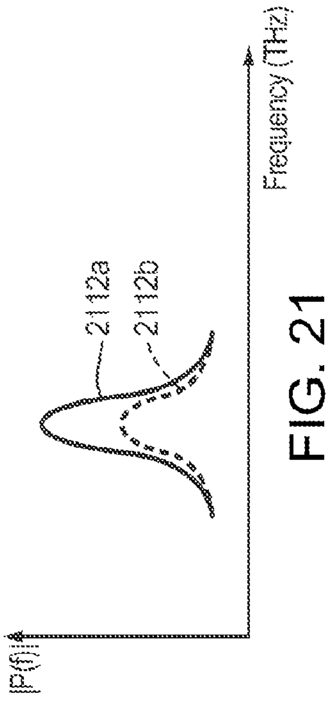
FIG. 21 is a power graph illustrating power differences between response curves with a narrowband frequency source light spectrum overlapping with a response curve.

The bio-functionalized element 116 is configured to effect a change in the spectral signature as a function of receipt or nonreceipt of the biomarker 118. Receipt of the biomarker 118 is illustrated schematically via an arrow 120. An example spectral signature 114*a* of the emitted light 112 is illustrated in FIG. 1 as a power spectral density of the emitted light 112 as a function of frequency, displaying a peak in the absolute value of the power spectral density at a particular frequency. A further example (changed) spectral signature 114*b* of the emitted light 112 is also shown, with a peak at a different frequency. This change in frequency is one example of a change in the spectral signature as a function of receipt or nonreceipt of the biomarker, where the spectral signature 114*a* can indicate absence (nonreceipt) of the biomarker 118, while the spectral signature 114*b* can indicate receipt of biomarker 118 by the bio-functionalized element 116. Nonetheless, other types of spectral signatures, and changes in spectral signatures, are within the scope of embodiments including this embodiment. For example, a spectral signature can include a power level, such as that illustrated by a peak height in the power spectral density illustrated in FIG. 21, while a change in the spectral signature can be a change in the power at the same frequency, as also illustrated in FIG. 21.

A combination of the light source 102 and the plasmonic nano-antenna 110 is configured to encode an optical communication signal into the emitted light 112. Transmission of the optical communication signal is illustrated in FIG. 1 via an arrow 124. Thus, a portion of the emitted light 112 is used for communication, and the combination of the light source 102 and plasmonic nano-antenna 110 is configured to transmit the optical communication signal, illustrated at 124, via the emitted light 112 exhibiting the spectral signature 114*a* or 114*b*, to a communication node 126 that is physically separated from the biosensor. Various configurations and parameters for the light source 102 and plasmonic nano-antenna 110 to achieve this communication are described hereinafter, both in connection with FIGS. 5-6 and in other portions of this description.

Figure 18A:
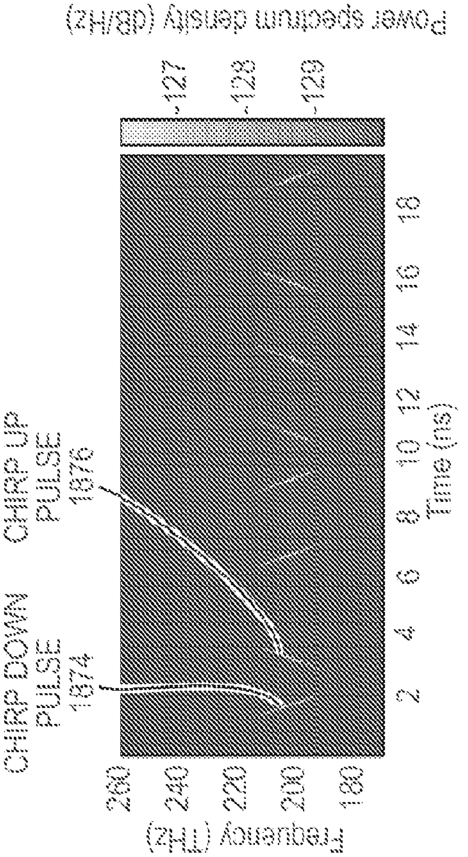
FIGS. 18A-18B are graphs showing a data packet (01001110) transmitted using chirp modulation method with no biomarker binding (FIG. 18A) and with biomarker binding (FIG. 18B).
Figure 18B:
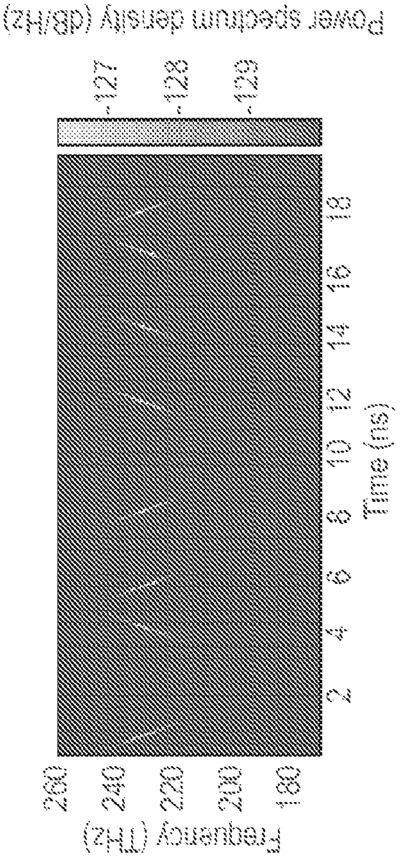

In one example, the optical communications signal encoding can include an encoded indication of whether the biomarker 118 is received by the bio functionalized element 116 (e.g., indicating whether a disease is present if the biomarker is a disease biomarker). However, any other type of information or data that are desired to be communicated from the biosensor 100 to the communication node 126 can also be encoded into the emitted light 112 additionally or alternatively. This option is represented and described hereinafter in part in connection with the optional "other data in" 164 illustrated in FIG. 1 and in connection with FIG. 14, for example. Thus, the optical communication signal transmission should be understood to be very flexible in the information that is carried, and it may include an indication of whether a biomarker is received, whether the living being 108 has the corresponding disease, any other optional information that may be gathered by the biosensor 100, or other data or information provided to the biosensor 100, or a combination thereof, for example. In one example, the encoding can be by means of chirp-up and chirp-down signals in the source light, interacting with the plasmonic nano-antenna 110 and appearing in the emitted light 112, as illustrated in FIGS. 18A-18B.

FIG. 1 further illustrates (using dashed lines) optional features of the biosensor 100 in particularly advantageous embodiments, including a detector 128, a modulator 134, and related details. As illustrated by a dashed arrow 130, indicating optional receipt of emitted light by the detector 128, the biosensor 100 can include the detector 128 and the detector can be configured to detect the emitted light 112 and to provide an output 132 that is indicative of the receipt or nonreceipt of the biomarker 118 by the bio functionalized element 116. An example of how the detector 128 may function, and of components that it can include, is provided in FIG. 13.

The emitted light 112 should be understood broadly to include any light, such as covering any wavelength or frequency range of the source light 104, that emanates from the plasmonic nano-antenna 110 as the light 104 is received by the plasmonic nano-antenna 110, and as changed or not changed by receipt or nonreceipt of the biomarker 118 by the bio-functionalized element 116. In one example, illustrated in FIG. 4, the emitted light includes light that is reflected from the plasmonic nano-antenna and is received by a detector via a light guide, while another component of the emitted light 112, directed elsewhere, is used as the optical communication signal transmission.

In some embodiments, different components of the emitted light 112 can have different spectral compositions. In one example, emitted light 112 that is reflected by the plasmonic nano-antenna 110 can have a power peak at a resonant frequency of the plasmonic nano-antenna 110, while emitted light 112 that is transmitted includes a valley in power spectral density at the same frequency position as the peak in the reflected light. In other embodiments, emitted light 112 that is transmitted through the plasmonic nano-antenna 110 can be used both for the optical communication signal transmission 124 and for detection by the detector 128.

As part of the optional features of the biosensor 100, the detector 128 provides an output 132 that is indicative of the receipt or nonreceipt of the biomarker 118 by the bio-functionalized element 116. This can be a Boolean value or can be represented by more complex data, such as a representation of the spectral signature of the emitted light, for example. The modulator 134 is configured to receive the output 132, as well as "other data in," represented by the arrow 164. The modulator 134 provides modulation, represented at arrow 136, of the light source 102. Combined with the plasmonic nano-antenna, this is further configured to encode the output 132 indicative of the receipt or nonreceipt of the biomarker into the optical communication signal 124.

Figure 20:
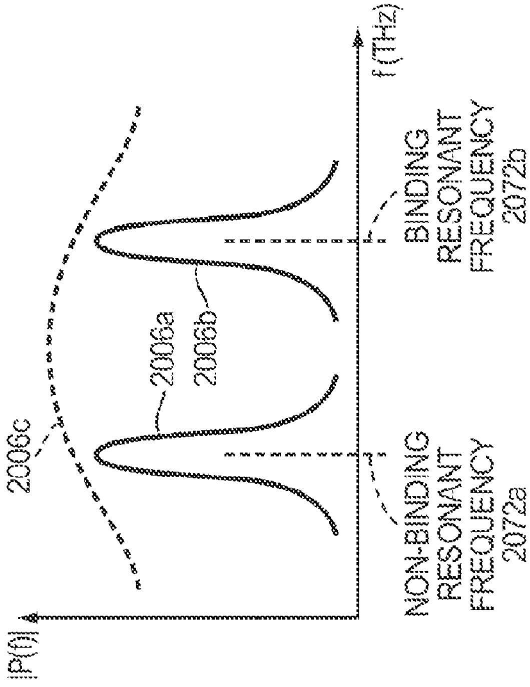
FIG. 20 is a graph illustrates a meaning of "broadband" as used herein.

The modulator 134 effects modulation in the source light, resulting in the corresponding modulation being exhibited in the emitted light 112. The combination of the light source 102 and the plasmonic nano-antenna 110 are thereby configured to encode the optical communication signal into the emitted light 112 via the corresponding modulation 136 exhibited in the emitted light. As described in connection with FIGS. 15A, 17A, 17B, 18A, and 18B, for example, the modulator can be further configured to cause the light source 102 to output the source light 104 as chirp-up and chirp-down pulses, and these chirp-up and chirp-down pulses can be used to encode the output 132, the other data in 164, or both into the emitted light 112 for purpose of the optical communication signal transmission 124. The source light can be broadband, including frequency components spanning a range of possible resonance frequencies of the plasmonic nano-antenna, as illustrated in FIG. 16 and FIG. 20, for example. Nonetheless, as one alternative, the source light 104 can include two narrowband frequency components corresponding, respectively, to a first resonance frequency of the plasmonic nano-antenna 110 in an attached state in which the biomarker 118 is available and attached to the bio functionalized element 116, and a second resonant frequency of the plasmonic nano-antenna 110 in a non-attached state in which the biomarker 118 is not available to the bio-functionalized element 116. In this case, the combination of the light source 102 and the plasmonic nano-antenna 110 can be further configured to encode the optical communication signal 124 into the emitted light 112 via a power difference between the two narrowband frequency components, with the power difference exhibited in the emitted light 112.

Figure 2:
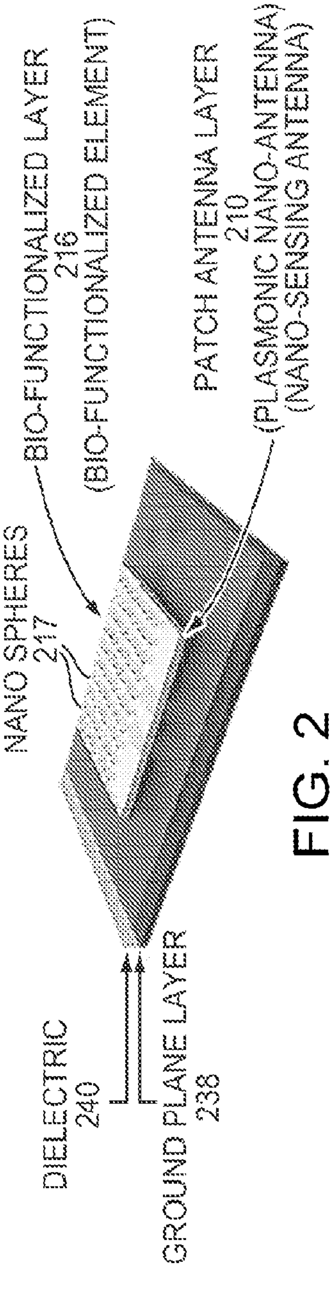
FIG. 2 is a perspective-view diagram illustrating an example plasmonic nano-patch antenna, configured for use as a bio-functionalized sensor, which can be used in various embodiments.

The bio-functionalized elements 116 can include a dielectric surface having nanosphere or microsphere particles situated thereon, as illustrated in example FIG. 2. The biomarker 118 can be a cardiac, cancer, Alzheimer's disease, or other neurological condition or other disease biomarker.

Figure 15B:
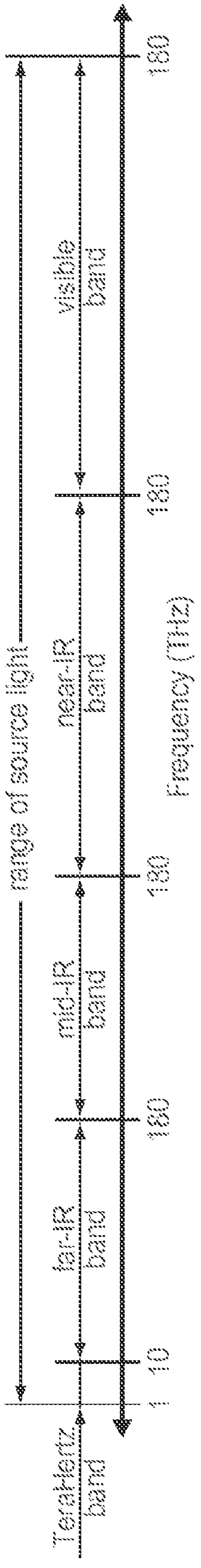
FIG. 15B illustrates the frequency range of "source light" as used herein in different embodiments.

As illustrated in FIG. 15B, "source light," as used herein, denotes frequencies including the range 1-770 THz. The source light 104 can generally cover a TeraHertz band, defined as covering 1-10 THz, a far-IR band, defined as covering 10-180 THz, a mid-IR band, defined as covering 180-250 THz, a near-IR band defined as covering 250-400 THz, a visible band defined as covering a range of 400-770 THz, or a combination thereof or a portion of one of these.

Figure 6:
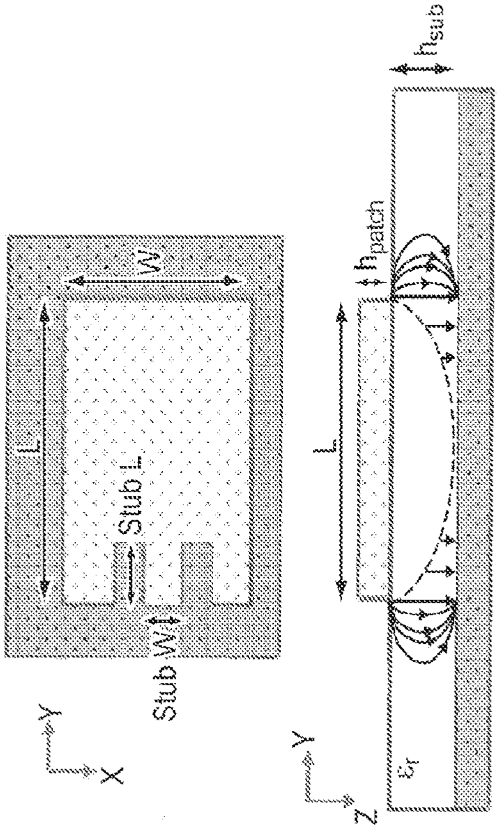
FIG. 6 is a cross-sectional view (bottom) and top view (top) of the geometry of a patch antenna (plasmonic nano-antenna) of various embodiment biosensors.
Figure 5:
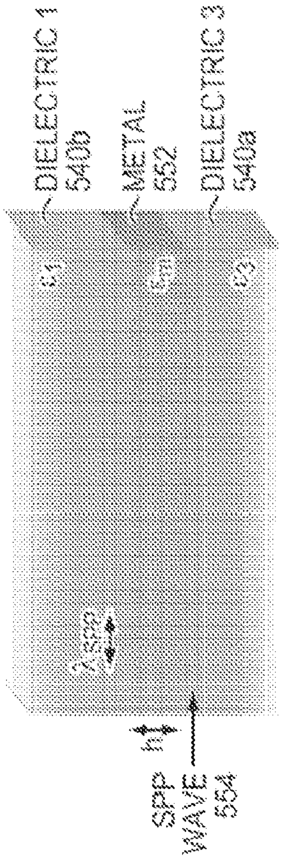
FIG. 5 is an illustration of SPP waves propagating at metal-dielectric-metal interfaces for a thin metal layer in various plasmonic nano-antennas forming part of embodiment biosensors.

The plasmonic nano-antenna 110 can include a gold or gold alloy layer situated between dielectric layers, as illustrated in FIGS. 5-6, for example.

FIG. 2 is a perspective-view diagram illustrating an example plasmonic nano-antenna 210, also referred to herein as a nano-patch antenna and as a nano-sensing antenna, and it is in the form of layer 210 that can be referred to as a patch antenna layer 210. The plasmonic nano-antenna 210 is configured for use in a bio-functionalized sensor (biosensor) such as the biosensor 100 of FIG. 1, by means of a bio-functionalized element 216 that is joined to the antenna 216. FIG. 2 illustrates the design of the nano-communicating and -sensing antenna. The bio-functionalized layer 216 includes nanospheres 217 that provide disease-specific biomarker detection. When in the proximity of a biomarker 118, the nanospheres 217 bind with it, changing the physical and electrochemical properties of the layer 216. On their turn, these trigger a change in the antenna frequency response of the plasmonic nano-antenna 210. The plasmonic 210 is situated on a dielectric layer 240, which is adjacent to a ground plane layer 238. In certain embodiments, microspheres can be used instead of the nanospheres 217.

Certain of these and additional features of embodiments are described hereinafter in the following order. In Sec. I, an introduction to the further subject matter, and context for this, is provided. Sec. II presents relevant related work focusing on the human tissue channel model for optical signals, plasmonic biosensors, bio-functionalization and joint communication and sensing. Sec. III presents a design of an embodiment optical nano-antenna. Sec. IV provides data evaluating performance of the designed embodiment nano-patch antenna as a biosensor. Sec. V presents a design of the chirp waveform signal to extract the sensing information and carry the data in certain embodiments. Sec. VI presents a channel model for understanding the sensor-sensor and sensor-wearable device interactions in certain embodiments. Sec. VII presents one detection mechanism that can leverage the chirp waveform and the antenna response for performing sensing detection along with joint communication packet decoding in certain embodiments. Sec. VIII describes communication link analysis for different scenarios and model factors such as channel and noise on the received signal and bit error rate. Sec. IX presents numerical analysis results showcasing results from the analytical and numerical models, and in Sec. X, highlights of key advantages and study results for embodiments are presented.

I. Additional Introduction and Context for Advantages of Embodiments

With technological advances in science and technology, we are in the most-connected era of human society history ever. We live in a society where information travels at the speed of light, and traveling is easier than it ever has been in history. In such a dynamic paradigm, early pathogen detection and diagnosis are the key to defer the next pandemic in such a connected world. Traditionally, pathogen detection has been performed by using several sensing mechanisms such as color-changing chemical titration, microscopy, spectrometry, and recent RNA/DNA-based detection methods.

In parallel to these techniques, plasmonic sensing is an upcoming sensing technology that promises unprecedented accuracy for biomarker detection. Plasmonic sensing leverages molecular interactions at the nanoscale and bridges that with the macro world using light as an information carrier. Light, i.e., electromagnetic radiation in the optical spectrum, is utilized because its small wavelength enables molecular scale interactions with matter. Plasmonic nanostructures are designed to couple the incident light into plasmonic waves on metallic-dielectric interfaces. These plasmonic surface waves are sensitive to the surface structure properties and are therefore leveraged for sensing. The surface is made biomarker selective using molecular engineering where a bio-functionalized molecular layer is deposited on this plasmonic surface. The bio-functionalized layer binds only to the biomarker of interest and offers very high selectivity. This unprecedented selectivity allows for accurate detection at an ultra-low concentration.

Despite the unique capabilities of plasmonic sensors for biomarker detection and selectivity, currently, bulky test equipment is needed to interrogate the sensors, limiting their practical application. In parallel to these advances in sensing technology, nano-structural engineering and nano-photonic designs are also advancing the optical technology to nanoscale applications. In the last decade, lasing devices with ultra-small footprints, on-chip waveguides, plasmonic waveguides, power-splitters, phase shifters, nano-antennas, and metamaterials have enabled unprecedented nano-photonic advancements. While most of these technologies aim at solving communication bottlenecks by enabling ultra-compact broadband communication, these can be tailored to support nanoscale sensing applications.

Besides light-based nano-sensing, nanoscale communication has become an emerging field that can be leveraged to communicate intrabody nanomachine to nanomachine or implanted nano-machine to wearable. For such communications, different technologies are proposed such as galvanic coupling, ultrasound waves, electromagnetic waves in radio frequency band, TeraHertz band, and optical band, as well as molecular communications. Together, the aim has been to enable an Internet of Nano-Bio Things that bridges the macro world in which we live with the biological world inside our body. This opens the door to unprecedentedly precise sensing of disease biomarkers and real-time recovery monitoring and, ultimately, the next wave in healthcare technology that bridges the nano-bio scale with the power of cloud computing through edge networks. Such systems promise timely diagnosis, real-time monitoring and will play a key role in early detection of infectious diseases and mitigating future pandemics. Nevertheless, while these technologies provide a roadmap for the future of Internet of Nano-Bio Things, the technological bridges that can translate these models into real nano-device designs have been missing.

Disclosed herein are biosensors and communication nodes that can include plasmonic nano-antennas that can also work as bio-functionalized sensors to bridge the gap of the nano-sensing device and nanoscale intra-body communications.

Figure 3:
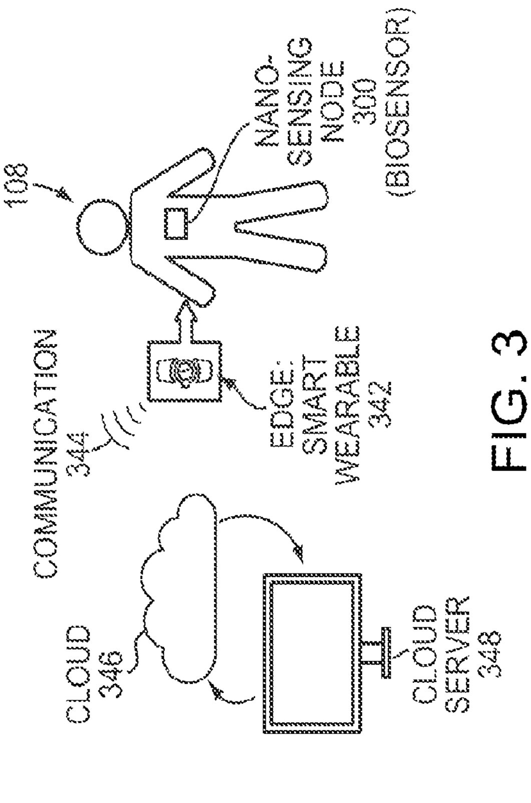
FIG. 3 is a schematic diagram illustrating an edge computing/networking environment with an embodiment device implanted in a living being and forming part of the Internet of Nano-Bio Things.
Figure 4:
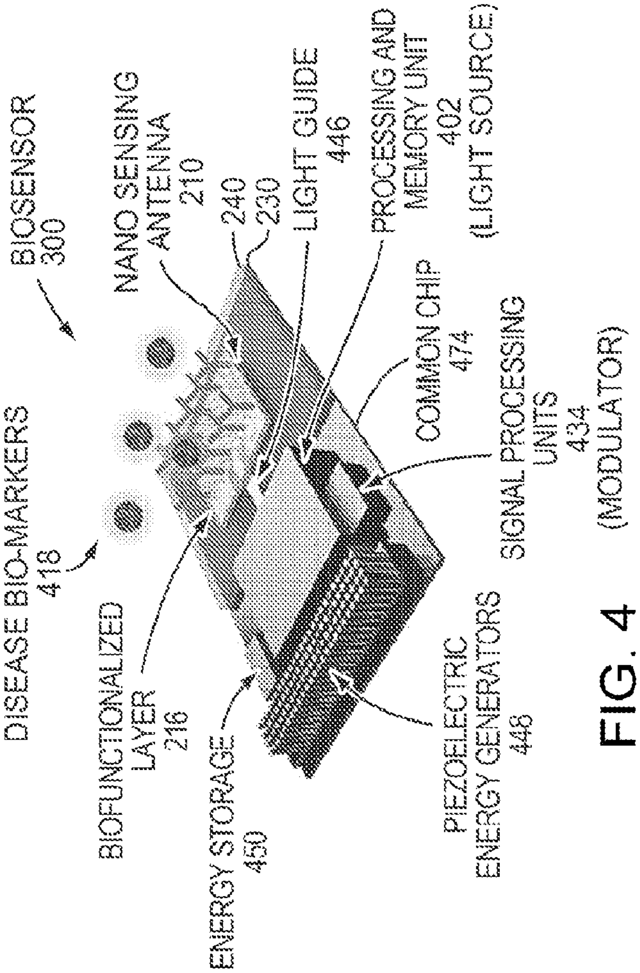
FIG. 4 is a perspective-view diagram of the biosensor illustrated in FIG. 3 and is configured to be implanted into the living being.

FIG. 3 is a schematic diagram illustrating an edge computing/networking environment with an embodiment device implanted in a living being and forming part of the Internet of Nano-Bio Things. An embodiment nano-sensing node (biosensor) 300, which is described in further detail in connection with FIG. 4, is implanted into the living being 108. The biosensor 300 performs both the sensing function and the optional detecting function as described in connection with FIG. 1 and can communicate the output 132 and/or "other data in" 164 to a smart wearable device 342 via the optical communication signal 124. In turn, the smart wearable device 342, which constitutes an example communication node that is physically separated from the biosensor 300, communicates with a cloud server 348, through a cloud environment 346, via a communication signal 344. The signal 344 can be Wi-Fi®, Bluetooth®, cellular signals, or other communication means known in the art of device networking.

FIG. 4 is a perspective-view diagram of the biosensor 300 illustrated in FIG. 3 and is configured to be implanted into the living being 108. The biosensor 300 has the basic functions of the biosensor 100 illustrated in FIG. 1, as well as detector and modulation functions given as optional in FIG. 1. The biosensor 300 includes a light source 402, which is also referred to herein as a processing and memory unit. The biosensor 300 also includes the plasmonic nano-antenna 210 described in connection with FIG. 2, which is situated on the dielectric 240, which is affixed to the ground plane layer 238, as also illustrated in FIG. 2.

All of these features and others are situated on a common chip 474 to achieve optical integration. Part of this integration is provided by a light guide 446. The light guide 446 conveys source light from the light source 402 to the nano-sensing antenna 210. Emitted light from the nano-sensing antenna 210 varies according to a spectral signature of the nano-sensing antenna 210, depending on whether a disease biomarker 418 is received at the bio-functionalized layer 210 that is joined to the plasmonic nano-antenna 210.

The emitted light that is reflected back from the nano sensing antenna 210 is further received at the processing and memory unit 402 via the light guide 446. The processing and memory unit 402 provides not only a light source, such as the light source 102 in FIG. 1, but also a detector, such as the detector 128 in FIG. 1 (not illustrated in FIG. 4). The signal processing unit 434 provides modulation function, as described in connection with the modulator 134 in FIG. 1. In addition, the biosensor 300 further includes piezoelectric energy generators 448 with energy storage 450, such that the entire biosensor 300 is self-powered.

With the light source 402, the plasmonic nano-antenna 210, the detector present in the processing and memory unit 402, and other components all mounted on the common chip 472, a high degree of integration and compactness is provided. With the plasmonic nano-antenna optically coupled to the light source via the light guide 446 on the common chip, the detector is further configured to receive the emitted light (not shown in FIG. 4) via the light guide 446, and the common chip 474 and related components thereon act as an integrated optical circuit.

The system 400 of FIG. 4 allows for simultaneous wireless biosensing and nano-communication in a compact footprint on a common chip. For sensing, the proposed antenna is coated with a bio-functionalized layer that binds to a disease-specific biomarker and changes the antenna response. To work in conjunction with nano-antenna, a chirp spread spectrum (CSS) may be used to extract the sensing response and simultaneously perform communication between intra-body nano-nodes and wearables. The wearable can perform computation at the edge to extract the sensing features and transmit the relevant data to the cloud as shown in FIG. 3. Along with system design, a detailed analysis of the sensing performance of the bio-functionalized nano-antenna and the bit error rate analysis of the communication link from nano-node to wearable using the CSS is provided.

II. Relevant Considerations

A. Human Tissue Model

Research groups have previously modeled human tissue as a channel for optical signal propagation. These works rely on experimental data and the spectrometric analysis of tissue types such as skin, blood, adipose, muscle, brain tissue, and melanin concentrations. While many of these measured properties help model human tissues to some degree, in reality these models have large variance and any multi-layer or bulk tissue model without some modification cannot perfectly fit all humans. This is because the composition of human body varies from person to person. However, a fair approximation can be made to guide the engineering design with factors such as layer thickness and concentration. The concentrations of factors such as fat, melanin content, and blood concentration affect the optical signal propagation. For the special case of optical communication at nanoscale, along with these factors, non-homogeneity of the tissues and cellular composition also affects the signal propagation making it even more challenging to predict the response. Some works have attempted to create models that aim to target such nanoscale communication links for cell-cell or nanomachine-cell interactions.

B. Plasmonic Biosensors

Plasmonic biosensors have been an active area of research in last decade and there has been a myriad of advances made in this field. Plasmonic biosensing relies on plasmon polariton waves which can be excited using a prism and coupling the light in reflection from the sensor. The surface of a plasmonic sensor is coated with bio-functionalized layer that binds to target molecule and changes structure resonance. This effect is then detected in reflection or transmittance to perform sensing. Plasmonic biosensing can be performed using different mechanisms: Surface plasmon resonance (SPR) sensing, localized surface plasmon resonance (LSPR) biosensing, Chiral plasmonic biosensing, Magnetoplasmonic biosensing, and Quantum plasmonic biosensing.

The LSPR biosensing is done using subwavelength particles, which, due to the small size, are more sensitive to their surrounding media properties. Traditionally, they have been used to enhance the spectroscopic measurements such as in surface-enhanced infrared absorption spectroscopy, surface-enhanced Raman scattering, surface-enhanced fluorescence, and by detecting a shift in absorption spectra (sensitive to surrounding molecules).

Chiral plasmonic biosensing relies on the fact that chiral symmetry causes different absorption for right-hand circularly polarized light and left-hand circularly polarized light. This difference can be leveraged at the plasmonic level to identify the mechanisms of chiral bioactivity in proteins. Chiral plasmonic has, therefore, become an active area of research to develop chiral sensitive plasmonic structures for sensing in visible and NIR region.

Magnetoplasmonics biosensing relies on magnetic nanoparticles and magneto-optical structures to amplify surface plasmon polariton waves. These merged effects of plasmonic with magneto-optics are called magnetoplasmonics. They have gained their popularity for in-vitro sensing and bio-imaging applications.

Quantum plasmonic biosensing tries to overcome the fundamental limit of plasmonic waves carrying information. By using the quantum properties of light, such as quantum correlation, and shielding, the information carried from the noise floor is defined by the shot-noise limit defined by the Heisenberg uncertainty principle. In addition to these types, there have been demonstrations of sensing based on functionalized graphene nanoribbon-based biosensors, bio-functionalized optical waveguide-based plasmonics sensors and bio-functionalized field effect transistor channel biosensors that leverage plasmonics to perform sensing.

C. Bio-Functionalization

Plasmonic biosensors are sensitive to their surrounding layers, and to make them sensitive to a particular biomarker, they need to be coated with a bio-functionalized layer. The binding process results in a change of physical properties such as refractive index, conductivity, or pH value, among others. These changes influence the resonance frequency of the SPR sensor. The successful coating of an SPR sensor with a bio-functionalized layer requires two main components, namely, a primer layer and a bio-functionalized layer. The primer binds to the metal surface of the sensor and allows the biomarker selective coating to bind reliably on the sensor.

Based on their type of binding, sensors can be classified into four categories: DNA-, immuno-, cell-, antigen- and imprinting-based sensors. DNA-based sensing lever-ages single-stranded DNA (ssDNA) and its affinity to bind with the virus. A layer of ssDNA with preserved reactivity towards the host-virus is deposited on the SPR. Such ssDNA layer is carefully designed to be stable and relies on nucleic acid hybridization. Peptide nucleic acids, which are structurally similar to DNA, have also proved to be a promising candidate for DNA detection.

Immunosensors rely on using the antigens created by the bodies in response to the virus for detection. These antigens have a higher affinity for the virus proteins and thus bind with them, similar to a lock-key mechanism. Such binding results in the change of the structural properties of the surface layer, which changes the response of the SPR sensor, thus allowing for the detection by an optical signal transmitted or reflected by the sensor. To reduce dependency on the immune-generated antigens, active research is going on to develop DNA and peptide aptamers that resemble immune-generated antigens, which have been demonstrated for the detection of viruses. Antigen-based sensors work on the principle of coating the surface with a virus, and when the antigens come in contact with the surface, they change the surface properties. For testing such sensors, antigens are extracted from an infected person's serum. These sensors are limited by the concentration of antigens produced by the person at different stages of infection. These types of sensors are currently limited to out-of-body testing in laboratory setups.

Cell-based sensors cover the surface of the sensor with the host cells. When the virus attaches and infects the cell, it causes the changes, thus providing the ability to analyze cytopathic effects. These sensors provide an alternative to studying viral infections other than hosts or animals.

Imprinting-based sensors rely on using the molecular imprinted polymers, which are synthetically designed to provide complimentary vacancies in the polymer matrix that allows for the deposition of the target antibody or virus on the surface. These perform similar to the biological methods of detection but improve on increasing reliability and function in harsh operating environments with re-usability and reduced cost.

Biosensors can be impacted by other elements besides their target biomarker. More specifically, while they might not chemically react, other blood components, including red and white blood cells and platelets, might obstruct the implant. Correspondingly, sensor defouling and reusability are currently at the center of several studies, and multiple different methods have been proposed, from ultrasonic cleaning to electrochemical defouling.

D. Joint Communication and Sensing

Joint communication and sensing have recently gained popularity in the context of 5G and even 6G networks. Mainly, in joint communications and sensing systems, the same hardware, the same spectrum, and ultimately, the same signals are utilized to both carry information from the transmitter to the receiver while performing radar, i.e., extracting information from the channel itself. These types of systems leverage properties of signal propagation for multipurpose applications. However, other sensing methods utilize the communication channel changes for sensing, such as optical fiber-based earthquake detection and waveguide-based optical sensing. With some known properties about the channel, they all rely on the spectrographic properties of the molecules composing the channel and try to predict the presence of a certain molecule based on its band of absorption. These systems rely on a relatively wide band transmitter and a sensitive detector that can sweep across the band of interest accurately for valid detection signals. Traditionally, these sensing measurements were performed by spectrometers, but with advances in device technology and the access to low-cost high-quality sources and detectors widely available for communications, these measurements can be performed using the communication equipment.

FIG. 5 is an illustration of SPP waves 554 propagating at metal-dielectric-metal interfaces for a thin metal layer 552. The metal layer 522 is situated between an upper dielectric layer 3 540*a* and a lower dielectric layer 1 540*b*.

III. Nano Antenna Design

Optical nano-antennas covering the 1-770 THz frequency range in some embodiments are functionally similar in some respects to their radio-frequency counterparts. They rely on the electromagnetic (EM) wave propagation length and the resonating structural parameters. However, materials such as metals, which are perfect electric conductors at radio frequencies, do not behave as perfect electric conductors at optical frequencies. These material properties influence the EM wave propagation inside the material and thus the overall geometry of the resonating structure.

A. Plasmonic Properties of Metals at Optical Frequencies

At optical frequencies, metals exhibit complex frequency-dependent conductivity. This complex conductivity arises/originates from the plasmon polariton waves on metal-dielectric interfaces. Plasmon waves are surface waves that exist in the electron cloud of the metal present on the metal-dielectric interface. These oscillations and their effect on the permittivity of the metal can be represented by the Drude-Lorentz model as:

$$\varepsilon_m = \left[\varepsilon_m(\infty) - \frac{\omega_p^2\tau_d^2}{1+\omega^2\tau_d^2} + j\frac{\omega_p^2\tau_d}{\omega(1+\omega^2\tau_d^2)}\right], \tag{1}$$

where $\varepsilon_m$ is the permittivity of the metal, $\omega_p$ is the plasma frequency of the material, $\tau_d$ is the electron relaxation time, $\varepsilon_m$ ($\vartheta$) is the high frequency dielectric constant and $\omega=2\pi f$ is the angular frequency.

Using this complex conductivity model, the propagation wave vector $k_{spp}$ can be calculated accounting for the dispersion along the structure as per equation:

$$k_{spp} = (\varepsilon_1\varepsilon_3 S_3^2 + \varepsilon_m^2 S_2 S_3)\tanh(S_2 h) + \varepsilon_m S_2(\varepsilon_3 S_1 + \varepsilon_1 S_3) \tag{2}$$

$$S_1 = \sqrt{\beta^2 - \varepsilon_1 k_0^2}, \tag{3}$$

$$S_2 = \sqrt{\beta^2 - \varepsilon_m k_0^2}, \tag{4}$$

$$S_3 = \sqrt{\beta^2 - \varepsilon_3 k_0^2}, \tag{5}$$

where $k_0=\omega/c$ is the free space vector, $\beta$ stands for the complex propagation constant parallel to the surface, $\varepsilon_1$ and $\varepsilon_3$ are the permittivity of the layers surrounding the metal sheet, and $\varepsilon_m$ is the permittivity of the metal as described in (1). Using $k_{spp}$, we can calculate the plasmonic wavelength using the relation:

$$\lambda_{spp} = \frac{2\pi}{\Re\{k_{spp}\}}. \tag{6}$$

At optical frequencies, $\lambda_{spp}$ governs the antenna design equations instead of the free space wavelength.

Therefore, it is established that the resonating frequency of our antenna is sensitive to not only the structure length but also to the surrounding material properties. This property can be harnessed for sensing. Sec. IV presents further details on the performance of such a plasmonic antenna as a sensor.

B. Optical Nano-Patch Design

Patch antennas have become a popular choice for design in modern wireless applications. One of the main advantages a patch antenna offers is its flat design which makes it suitable to be produced on a mass scale with reliable manufacturing processes such as integration with printed circuits. Even at the nanoscale, flat designs allow for easier fabrication by using techniques such as metal deposition, masking, and etching.

A patch antenna usually includes three main components, a meticulously designed resonating patch, a ground plane, and a dielectric material in between the patch and ground plane. The geometry of patch is a deciding factor for its resonating frequency, and for perfect conductors is usually in the range of $L>\lambda_0/3$ and $L<\lambda_0/2$, where $\lambda_0$ is the free-space design wavelength. However, the E-field distribution between ground plane and the patch is affected by the dielectric material properties. Therefore, a patch antenna resonance is highly sensitive to the surrounding dielectric properties. Patch antennas are usually designed to function as broadside radiators, radiating maximum power perpendicular to the antenna plane. However, with a careful selection of excitation mode and design parameters, they can also be designed as end-fire radiators, radiating maximum power in the direction of the antenna plane.

FIG. 6 is a cross-sectional view (bottom) and top view (top) of the geometry of a patch antenna. FIG. 6 illustrates antenna length, width, and thickness parameters referred to in the modelling description hereinafter.

Unlike dipole antennas, there is no closed-form expression to dictate the patch antenna geometry. However, there are models that approximate these dimensions, such as cavity model, but these models rely on assumptions that antenna material is a perfect electric conductor, and the models fail to account for phenomena such as plasmonic waves on the antenna-dielectric surface and Fabry-Perot effect from the patch-ground plane cavity. Due to the complexity of formulating these models analytically, FEM analysis is often used as a standard practice to design and predict patch antenna performance.

Figure 7:
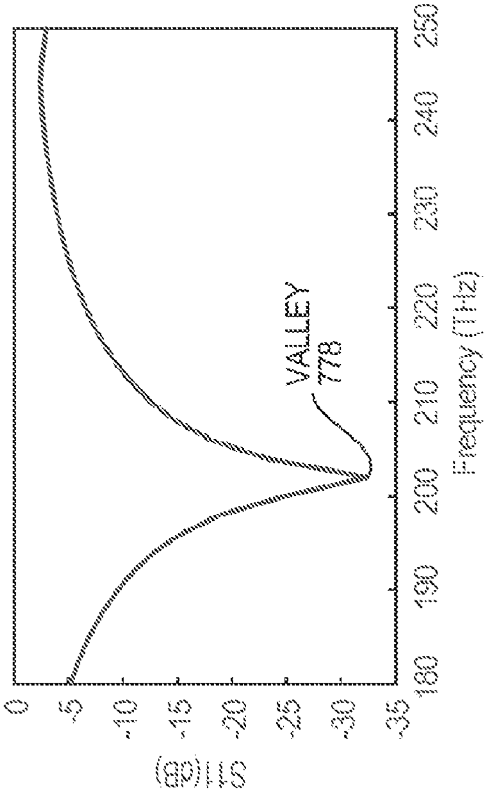
FIG. 7 is a graph illustrating S11 parameter of the referenced nano-patch described above, designed to operate with a resonant frequency near 200 THz.

The inventors have used finite-element methods (FEM) with COMSOL Multiphysics to design and model patch antennas at optical frequencies. The active antenna element and the ground plane have been modeled with the complex-valued material properties of gold. The dielectric substrate sandwiched between the ground plane and the patch is chosen to be of dielectric constant $\varepsilon_r=4$ (~ Dielectric constant of $SiO_2=3.9$). The antenna performance parameter S11 has been utilized as the objective function, parametric sweeps have been performed across antenna length, width, and thickness, parameters illustrated in FIG. 6, to minimize the reflection losses of design frequency and maximize radiated signal. An operating frequency of 200 THz has been selected, which corresponds to the popular telecommunication wavelength of 1500 nm, commonly adopted in fiber-optical systems and for which many of the aforementioned technologies have been developed. A set of final preferred design parameters is presented in Table I, and the resulting S11 parameters are shown in FIG. 7.

TABLE I

Design parameters of an optical gold nano-patch antenna resonant at 200 THz.

| Parameter | Value |
|---|---|
| Patch Length | 370 nm |
| Patch Width | 300 nm |
| Stub Length | 60 nm |
| Stub Width | 10 nm |

TABLE I-continued

| Design parameters of an optical gold nano-patch antenna resonant at 200 THz. | |
|---|---|
| Parameter | Value |
| Substrate Thickness | 50 nm |
| Antenna Thickness | 20 nm |
| Plasma Frequency | 13.35 PHz |

FIG. 7 is a graph illustrating S11 parameter of the referenced nano-patch described above, designed to operate with a resonant frequency near 200 THz. FIG. 7 also illustrates an example valley 778 indicating a resonant frequency of the described nano-patch antenna (plasmonic nano-antenna), which is a feature that can be referred to herein as a spectral signature of the plasmonic nano-antenna in emitted light that is emitted from the plasmonic nano-antenna upon receiving source light. Both peaks and valleys in power spectral densities, S11 parameters in dB units, and the like can be used to characterize spectral signatures of particular embodiment plasmonic nano-antennae.

IV. Nano-Patch Antenna as a Biosensor

A biosensor is basically a transducer that converts one form of bio-signal into another form which can be extracted and analyzed to perform detection. Most existing sensors convert the measured bio-signal into a change in properties such as electric/optical conductance, reflected signal, or chemical binding properties. Localized surface plasmonic sensors can transduce the detection results into a difference in their resonating frequency, which can be read in reflection, transmittance, or conductance. To perform detection, these sensors can be coated with a bio-functionalized layer that binds to the biomarkers of interest. This binding results in a change in their surface properties, which affects the propagation of plasmonic waves on the sensor surface.

Generally, an antenna is designed to resonate at the desired frequency. However, in the case of a plasmonic antenna, this frequency can significantly change based on the properties of its surrounding material. This phenomenon offers an unprecedented way to accurately sense the environment with an existing antenna geometry. By bio-functionalized the antenna itself, when the target biomarker is present, both the electrical properties of the antenna building material and the thickness itself change. By tracking those changes, detection is performed.

Modeling a particular biomarker and the corresponding bio-functionalized layer would require an extensive study of the material properties, which is part of many ongoing works. Meanwhile, to analyze the detection performance of the indicated, preferable designed patch antenna, these effects are modelled in FEM analysis with a parameter sweep, as described in following.

Figure 8A:
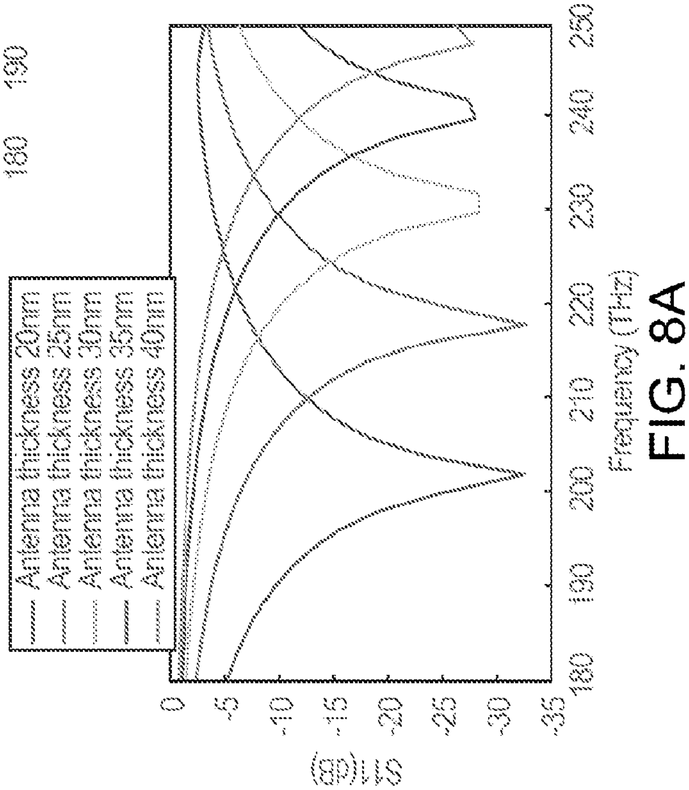
FIGS. 8A-8B are graphs generally showing sensing performance analysis of the designed optical patch antenna noted above, which is an example of those that may be used in embodiments.
Figure 8B:
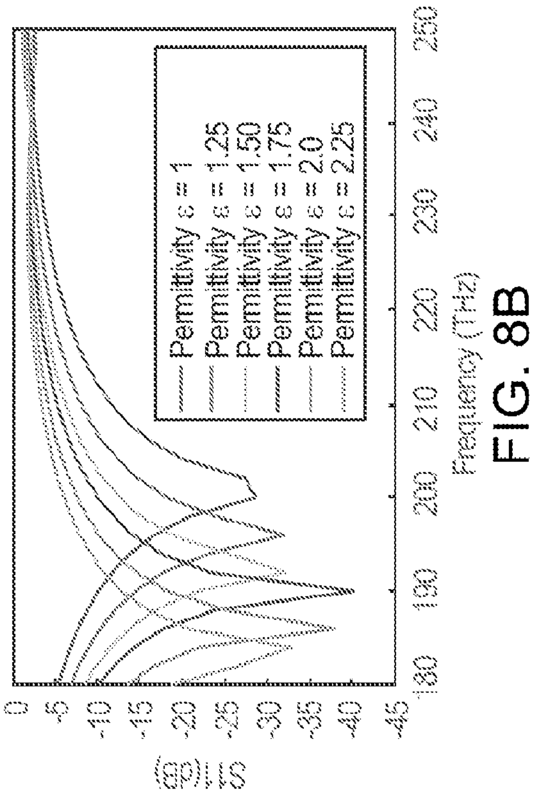

FIGS. 8A-8B are graphs generally showing sensing performance analysis of the designed optical patch antenna noted above, which is an example of those that may be used in embodiments. These results demonstrate the ability of the designed optical nano-patch antenna to function as a biosensor, for the following specific reasons.

FIG. 8A is a graph presenting the impact of change in the antenna patch thickness on the resonant frequency of the antenna. Particularly, it shows the S11 parameter as a function of frequency for different antenna top layer thickness $h_{patch}$. Patch thickness is varied in steps of 5 nm, and the results demonstrate that the antenna's resonating frequency is highly susceptible to these minor changes in thickness.

FIG. 8B is a graph illustrating the effect of change in the dielectric properties ((=1-2.25) of the material on top of the patch affecting the resonating frequency of the antenna. Particularly, it shows the S11 parameter as a function of frequency for different top dielectric layer permittivities.

V. Antenna Excitation Signal Waveform Design

To extract the sensing information from the antenna, a wide-band waveform that spans all the possible resonant frequencies of the antenna when sensing should preferably be used. Considering the limited capabilities of a nanomachine, a frequency-sweeping chirp signal can be advantageously used. The simplest chirp waveform is the linear chirp signal, in which the frequency increases with time (up chirp) or decreases with time (down chirp). Chirp waveforms have been widely used for sensing, as the multi frequencies translate to multi-resolution sensing. Chirp waveforms offer several advantages for communications, such as immunity to channel frequency selectivity.

A chirp signal in time domain is defined as $$x(t) = \sin(\phi_0 + 2\pi f(t)t), \tag{7}$$

where $\phi_0$ is the initial phase of the signal and $$f(t) = Ct/2 + f_{start}, \tag{8}$$

where C is the chirp rate/slope and $f_{start}$ is the starting frequency. For linear chirp signals, $$C = (f_{stop} - f_{start})/T, \tag{9}$$

where $f_{stop}$ is the chirp stop frequency and $f_{start}$ is the chirp start frequency and T is the time of sweep.

When this sweeping chirp signal is transmitted through the antenna, the antenna response is imprinted on it, which can be used for sensing. The power spectral density $P_t$ of the imprinted transmitted signal is given by $$P_t(f) = P_{chirp}(f)(1 - |R_{ant}(f)|^2, \tag{10}$$

where $P_{chirp}$ is the power spectral density of generated chirp signal and $R_{ant}$ is the antenna input reflection coefficient or S11 parameter and depends on the sensed information, as described in Sec. IV.

VI. Channel Model

To model the communication performance for the proposed joint sensing and communication system effectively, an accurate channel model should be used. For this analysis, two scenarios are considered: A) Nano-sensor to nano-sensor link, and B) Nano-sensor to wearable link. The channel losses can be classified as the combination of the following phenomena:

Reflective loss: This is the result of the refractive index mismatch between the different tissue layers in the body. These losses can be modeled using the following equation:

$$L_{Ref}(\lambda) = \left(\frac{|n_1(\lambda) - n_2(\lambda)|}{n_1(\lambda) + n_2(\lambda)}\right)^2, \quad (11)$$

where $n_1$ and $n_2$ stand for the refractive index of Layer 1 and Layer 2, respectively. The refractive index of different tissue types for the wavelengths $\lambda$ of interest is summarized in Table II.

TABLE II

Refractive index of tissue in optical band 400 nm-2000 nm.

| Layer | Value(n) |
|---|---|
| Air | 1 |
| Skin tissue [37], [101] | 1.41 |
| Adipose tissue [37], [102] | 1.44 |
| Blood (98% oxygenated) [103] | 1.37 |

Scattering and absorption loss: These losses account for the absorption and scattering from the medium. A general calculation for scattering and absorption losses can be performed using the equation:

$$L_{ScaAbs}(\lambda, d) = \exp((\mu_{scr}(\lambda) + \mu_{abs}(\lambda))d), \quad (12)$$

where $\mu_{scr}$ is the scattering coefficient, $\mu_{obs}$ is absorption coefficient and dis the distance/layer thickness. The absorption and scattering properties (user and Jabs) are compiled from literature. For the 400 nm-2000 nm band, plots of absorption and spreading coefficients for blood (for 98% oxygenated blood), adipose tissue, and skin (for Caucasian skin) are shown in FIG. 9A, FIG. 9B, and FIG. 9C, respectively.

Figure 9B:
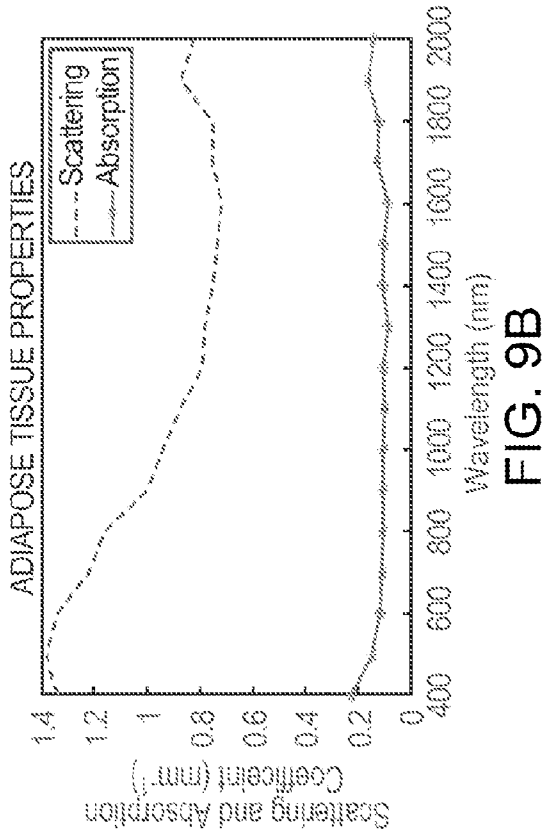
FIGS. 9A-9C are graphs illustrating scattering and absorption properties of different human tissue layered channels over a limited optical band of 400-2000 nm, for modelling purposes.
Figure 9A:
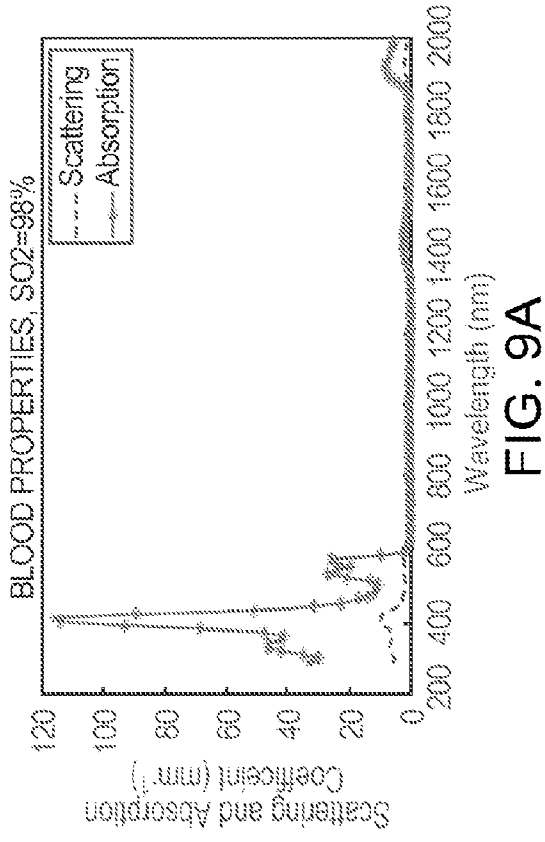
Figure 9C:
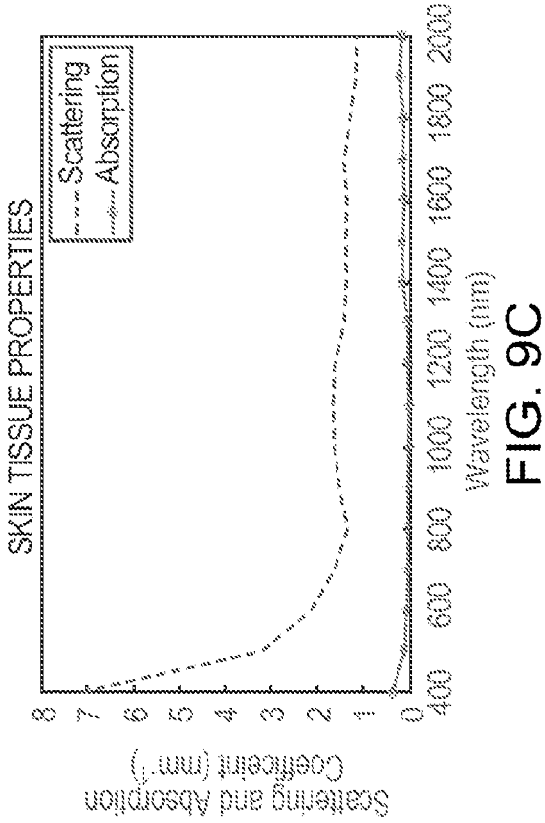

FIGS. 9A-9C generally are graphs illustrating scattering and absorption properties of different human tissue layered channels over a limited optical band of 400 nm-2000 nm, for purposes of the above-noted modelling. FIG. 9A is a graph illustrating scattering and absorption coefficient of whole blood. FIG. 9B is a graph illustrating scattering and absorption coefficient of adipose tissue. FIG. 9C is a graph illustrating scattering and absorption coefficient of skin tissue.

Spreading loss: This captures the fact that the signal propagates as a wave and spreads into the medium. This can be calculated using the equation:

$$L_{Spr}(\lambda, d) = \left(D\left(\frac{\lambda^2}{4\pi}\right)\left(\frac{1}{4\pi d^2}\right)\right)^{-1}, \quad (13)$$

where d is the distance from the radiation source, D is the directivity gain ($D=4\pi/\Omega_4$), for a point directional source such as a laser emitting with the radiated beam angle $\theta$ and $\phi$, the directivity D can be expressed as:

$$D = \int_{\theta=0}^{\Delta\theta}\int_{\phi=0}^{\Delta\phi} \sin\theta d\phi d\theta = \Delta\phi(1 - \cos\Delta\theta). \quad (14)$$

Total loss: All the previous losses in dB can be added to obtain the total loss suffered by the signal as:

$$L_{total}(\lambda, d)[\text{dB}] = 10\log(L_{Ref}(\lambda, d)L_{ScaAbs}(\lambda, d)L_{Spr}(\lambda, d)). \quad (15)$$

This total channel loss is frequency dependent and can be used to calculate the channel transfer function (H(f)).

A. Sensor to Sensor

For the sensor-to-sensor channel model, the sensors are assumed to be in different tissues, and thus we can create multiple cases. For the present analysis, presented are analytical calculations for two cases: Blood and Adipose (Fat) tissue.

Figure 10A:
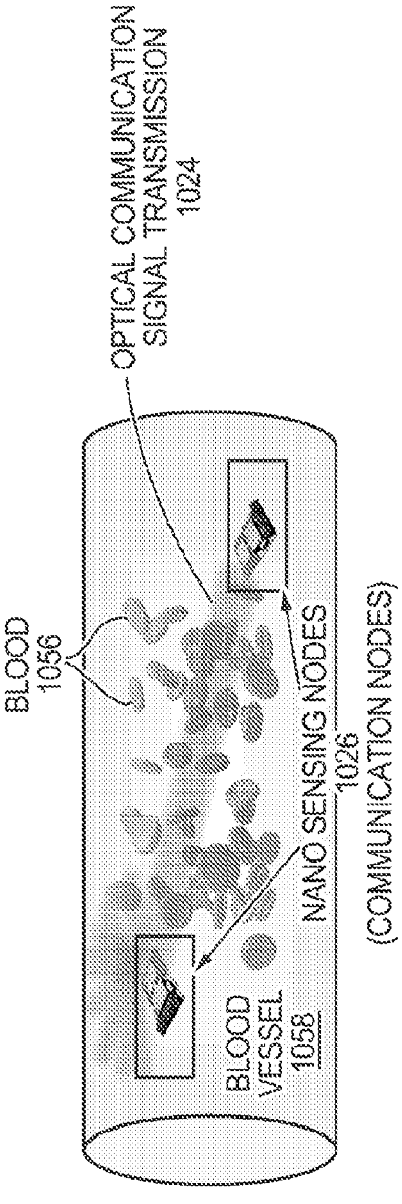
FIG. 10A illustrates a blood vessel with two embodiment biosensors flowing therein and configured for communication with each other.

Case 1 is to imagine the sensors are flowing in the bloodstream, as shown in FIG. 10A, with blood as channel.

FIG. 10A illustrates a blood vessel 1058 with blood 1056 flowing therein and two biosensors 1026 flowing therein, which may also be referred to as nano-sensing nodes or communication nodes, since they perform both of these functions. For this case of sensor-to-sensor communication through blood, the communication nodes 1026 should be understood to be configured to communicate with each other through the blood while being physically separated from one another. An optical communication signal transmission 1024 is sent from one node to the other node using light emitted from a plasmonic nano-antenna, as described in connection with FIG. 1. In this scenario, with two sensors flowing through the blood vessel, the sensors 1026 flowing through the blood vessel are an example of "implanted into a living being" as used herein. Thus, "implanted into," as used herein, can include both mobility and immobility in the living being, depending upon the specific application.

Figure 10B:
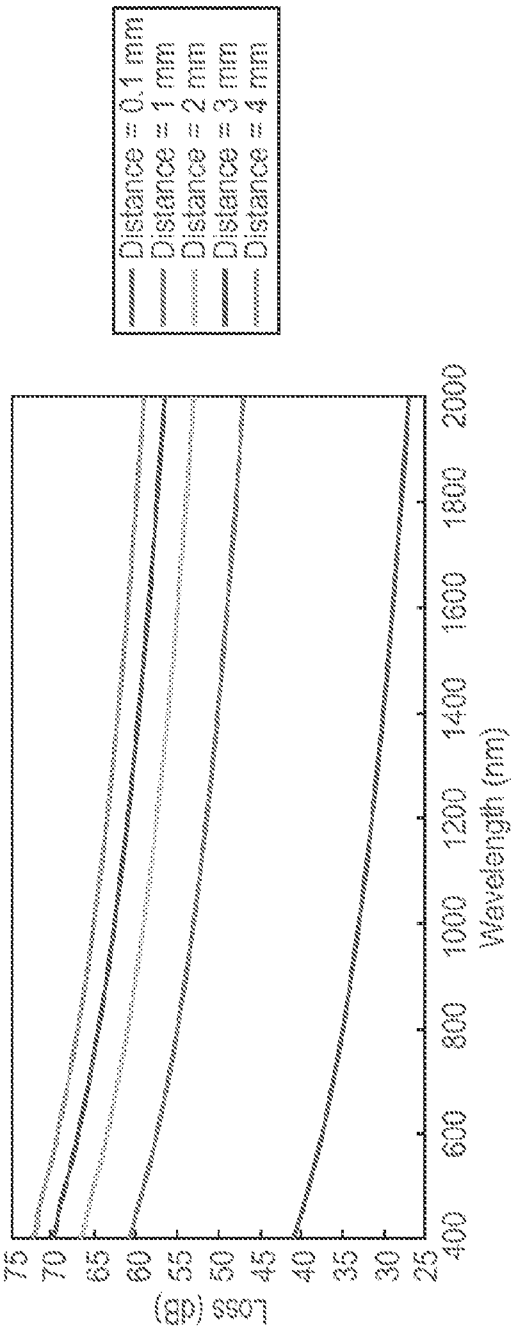
FIG. 10B is a graph illustrating total channel loss computed for the sensor-to-sensor link in blood, illustrated in FIG. 10A, for different inter-node distances.

FIG. 10B is a graph illustrating total channel loss computed for the sensor-to-sensor link in blood, illustrated in FIG. 10A, for different inter-node distances.

In case 1, the channel can be modelled as per the optical properties of blood as shown in FIG. 9A to compute scattering and absorption loss. Then total loss can be computed using (15), which is shown in FIG. 10B. For modeling the channel response, we accounted for the part where we used the distance as the main factor, for such high frequencies and the bandwidth, the effect of relative flow and speed difference will be minimal. Hence, the attenuation of the signal by the channel itself is the major factor affecting the signal, and the model follows that. However, to expand the model into a more practical application, an application-specific model should be developed to account for the right variables of mobility and CSI to predict performance.

Figure 11B:
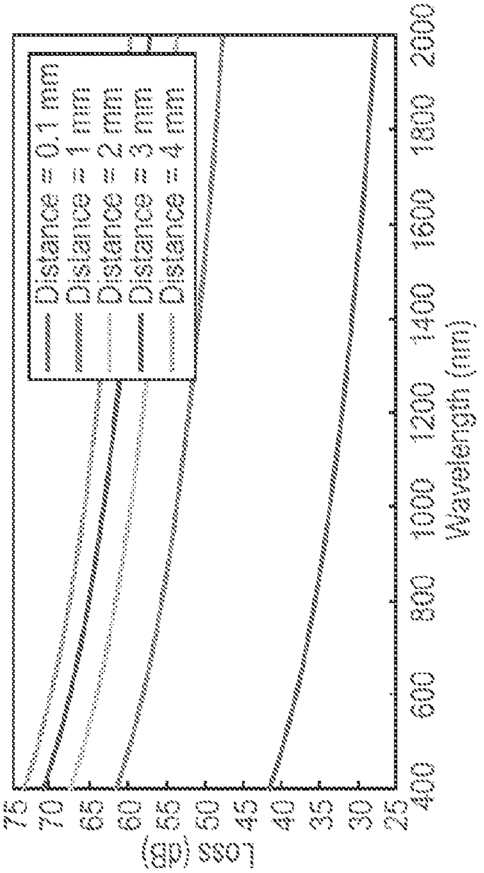
FIG. 11B is a graph illustrating total channel loss computed for the biosensor-to-biosensor link case illustrated in adipose tissue for different inter-node distances between the biosensors of FIG. 11A.
Figure 11A:
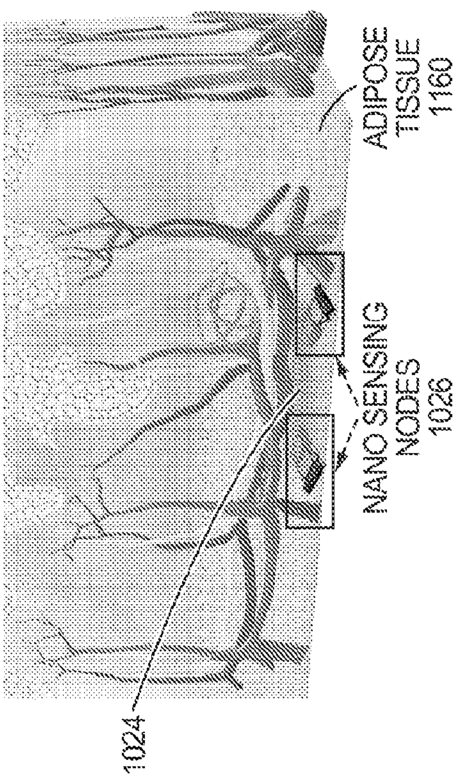
FIG. 11A is a diagram illustrating embodiment biosensors implanted into tissue, with a communication channel of adipose tissue separating them.

Case 2 is when embodiment biosensors are implanted in the fat layer of the human tissue and there is an adipose fat layer between them, as shown in FIG. 11A. Using the adipose tissue properties from FIG. 9B and Table II, the total loss can be calculated using (15). This loss is plotted in FIG. 11B for different distances.

FIGS. 11A-11B generally show the sensor-sensor communication scenario with adipose tissue as the communication channel between the biosensors.

FIG. 11A is a diagram illustrating embodiment biosensors 1026 (also referred to as nano-sensing nodes) acting as communication nodes since they are configured to communicate with each other as described hereinabove, implanted into a tissue of a living being and physically separated from one another, with a communication channel 1024 of adipose tissue 1160 separating them.

FIG. 11B is a graph illustrating total channel loss computed for the biosensor-to-biosensor link case illustrated in adipose tissue for different inter-node distances between the biosensors 1026.

B. Sensor to Wearable

For the sensor-to-wearable communication, the bulk tissue layered model should be considered. For this analysis, the bulk tissue can be considered to be a collection of different layers, and collective losses from each layer can be determined. For the multi-layer model, the different thickness of the tissue layer used are as follows: Air gap=1 mm, Skin tissue=1 mm, Adipose tissue=(0.1 mm-5 mm), Blood=0.25 mm.

Figure 12B:
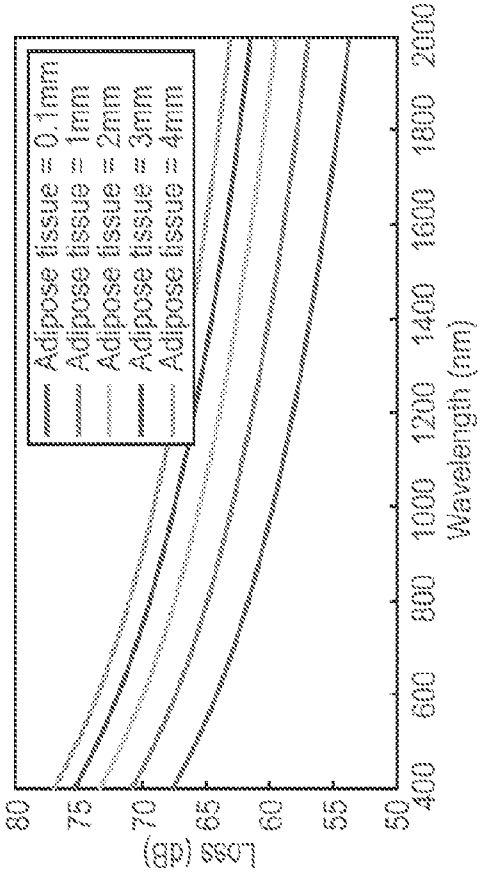
FIG. 12B is a graph illustrating total channel loss computed for wearable-to-biosensor link through multi-layer tissue model with different thickness of adipose tissues in the communication case illustrated in FIG. 12A.
Figure 12A:
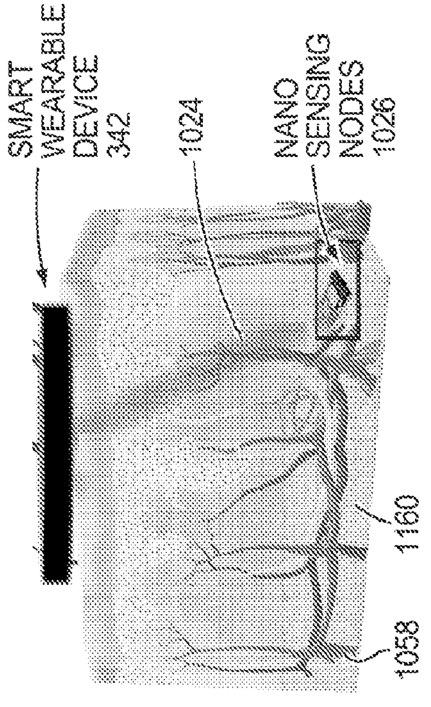
FIG. 12A is a graphical illustration showing implanted biosensor-to-wearable communication.

FIG. 12A is a graphical illustration showing biosensor-to-wearable communication from the biosensor (nano-sensing node or communication node) 1026, implanted into tissue of a living being, through different layers of skin tissues. The communication is from the implanted biosensor 1026, via an optical communication signal 1024 similar to that described in connection with FIG. 1, to the wearable device 342 outside of the tissue of the living being.

FIG. 12B is a graph illustrating total channel loss computed for wearable-to-biosensor link through multi-layer tissue model with different thickness of adipose tissues in the communication case illustrated in FIG. 12A. Losses from different tissue as per the model shown in FIG. 12A are calculated and presented in FIG. 12B with a common case of different adipose tissue thicknesses. On comparing results from FIG. 10, FIG. 11, and FIG. 12, it can be observed that the losses for a particular distance are close. First the vertical graph scale is logarithmic to highlight clearly the change. For reference, a 3 dB loss is half the power. And second, overall it is observed that spreading loss accounts for majority of the computed loss for the distance. For the given distance range of mm, comparing that to wavelength of few nm, it is very large. Assuming unidirectional antenna and no gains, these losses account for majority of loss. For example, ~64 dB of spreading loss is calculated from 0.1 mm of distance, assuming no gains and unidirectional radiators.

VII. Example Detection Mechanisms

A generated wideband chirp signal, illustrated in FIG. 16, can be transmitted through an embodiment plasmonic nano-antenna. During transmission, the antenna frequency response is imprinted onto the signal, which now carries the information of the antenna resonant frequency. Thus, this is one manner in which the emitted light from the plasmonic nano-antenna can exhibits a spectral signature of the plasmonic nano-antenna. Simply stated, the maximum power of the transmitted signal is at the antenna resonant frequency. As described in Sec. IV, for an antenna working as part of a biosensor, the shift in resonant frequency plays a significant role. Thus, a mechanism to detect the peak power of the received signal is needed to extract the sensing information. Detection of peak power can be performed using different approaches. A wideband power spectrum of the received signal can be plotted and used to detect peak power. However, the computational complexity of such a mechanism makes it a challenge to implement in a nanomachine.

Figure 13:
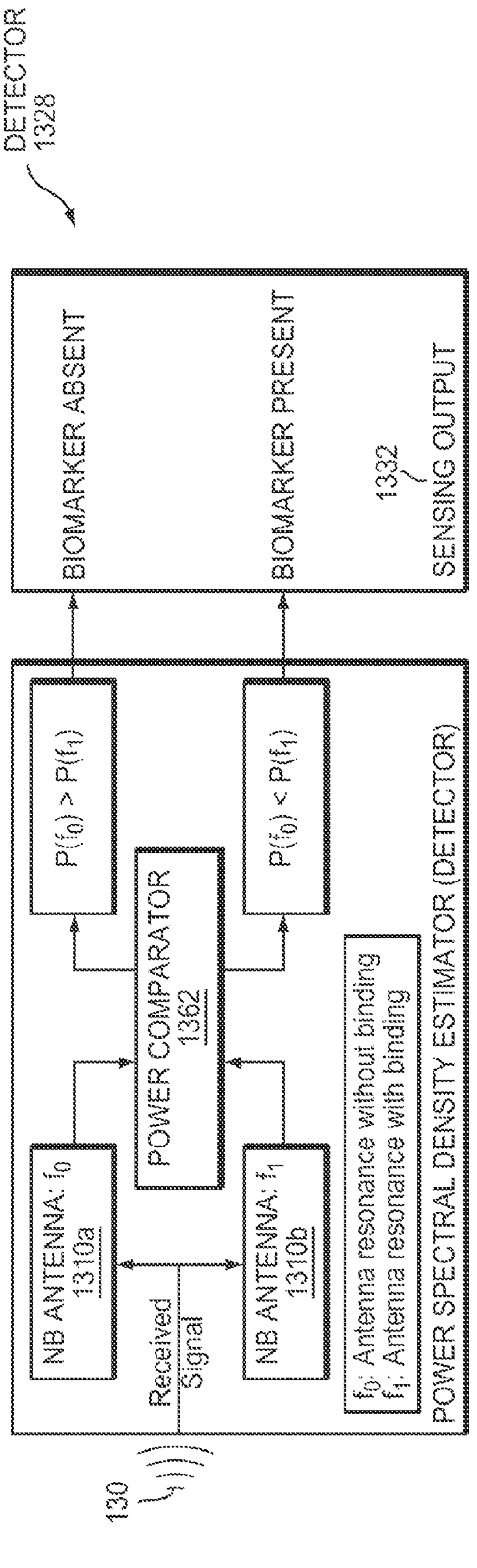
FIG. 13 is a block diagram illustrating a comparative detector that can be used advantageously in embodiment biosensors and communication nodes.

Instead of using the plotting approach and detecting peak power, embodiments biosensors and communication nodes can incorporate a much easier and less computationally intensive method, as illustrated in FIG. 13.

FIG. 13 is a block diagram illustrating a detector 1328 that is within the scope of embodiments encompassed by the detector 128 illustrated in FIG. 1 and can be used advantageously in embodiment biosensors and communication nodes for the reasons noted above. The detector 1328 includes a power spectral density estimator 1328 that operates as follows. Emitted light 130 that is emitted from a plasmonic nano-antenna either at the same node or a different node as the detector 1328 is received at the detector 1328. The received emitted light is passed directly through the two narrowband patch antennas 1310*a* and 1310*b* having respective resonant frequencies, ($f_0$), a non-binding frequency of the patch antenna, and ($f_1$), a binding frequency ($f_1$) of the patch antenna.

The received signals from the narrowband antennas are then fed to a power comparator 1362. If the power at $f_0$ is greater than the power at $f_1$, it can be deduced that the targeted biomarker is absent. However, if the power received at $f_1$ is greater than the power at $f_0$, then the conclusion is that the targeted biomarker is present. According, the detector 1328 uses multiple antenna elements and a power comparator setup similar to those proposed in cooperative spectroscopy. In this manner, calculating sensing output in a nanomachine with the detector 1328 can be facilitated and simplified very advantageously.

Figure 14A:
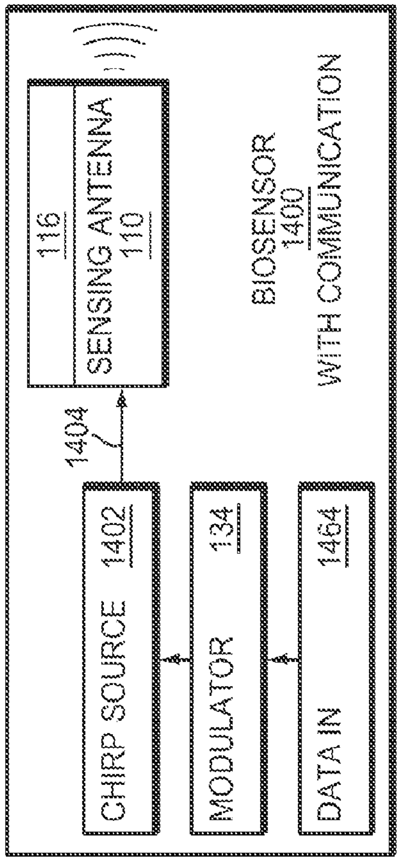
FIG. 14A is a block diagram illustrating an particularly advantageous embodiment biosensor with communication encoding.

FIG. 14A is a block diagram illustrating an particularly advantageous embodiment biosensor 1400 with communication encoding. In addition to the plasmonic nano-antenna 110 (also referred to as a "sensing antenna") and joined bio-functionalized element 116, the biosensor 1400 includes a chirp light source 1402 and the modulator 134 illustrated as optional in FIG. 1, for controlling the chirp light source to produce frequency-swept source light 1404 and chirp-up and chirp-down encoding in emitted light 1424, as described further hereinafter. Data in 1464 can include the sensing output 1332 or other data, such as additional spectral information or indications from other biosensors whether biomarkers have been detected at their respective locations.

Figure 14B:
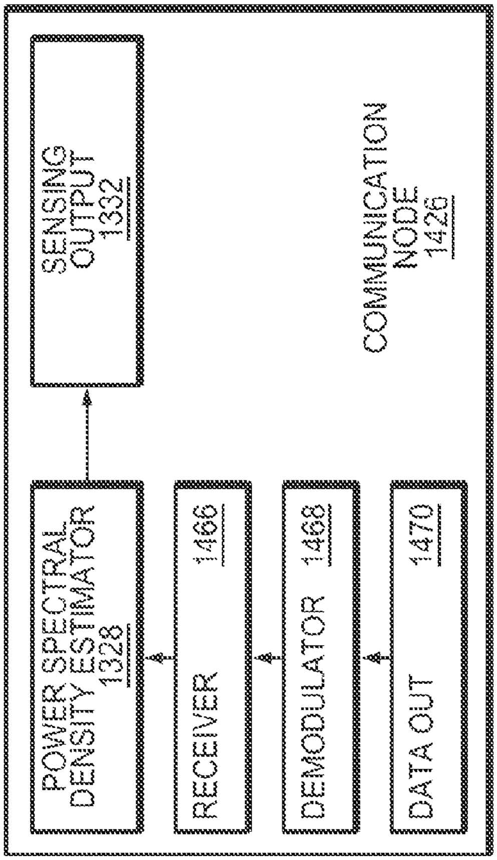
FIG. 14B is a block diagram illustrating a particularly advantageous embodiment communication node that combines sensing detection and data detection.

FIG. 14B is a block diagram illustrating a particularly advantageous embodiment communication node 1426 that combines both the functions of sensing detection of the detector 1328 of FIG. 13 and data detection from an encoded communication signal from another communication node, such as the biosensor 1400, with both functions performed in parallel using the same emitted light 1424 with data encoded therein. The detector (power spectral density estimator) 1328 acts on the emitted light 1424 as described in connection with FIG. 13 to produce the Boolean sensing output 1332. In parallel, a receiver 1466, receives a portion of the emitted light 1424 and converts it to an electronic signal. A demodulator 1468 receives the modulated electronic signal and produces data out 1470 to complete the receipt of information representing the data in 1464. In this manner, embodiment biosensors and communication nodes can provide efficient, compact sensing and communications. Advantageously, the sensing, sensing output, and data demodulation functions may be combined in a single biosensor that both determines its own sensing output, sends encoded communications to a physically separated communication node such as the node 126 of FIG. 1 or the nodes 1026 of FIG. 10 or FIG. 11A or the smart wearable device 342 of FIG. 12*a*, and decodes/demodulates to receive data from other communication node(s) such as other biosensors sending optical communications using emitted light emitted from a plasmonic nano-antenna. This sensing mechanism can be implemented parallel to the communication system, as shown in FIG. 14. Thus, communications and sensing can be simultaneously performed in the system.

VIII. Communication Link Model

With all the building blocks already defined, the communication link is modeled as follows.

A. Transmitter

A chirp signal is generated as per (7) and radiated by the antenna. Antenna reflection coefficient can be used to derive the antenna transfer function $H_{ant}(f)$ and transmitted signal can be as $X_{transmit}(f)=X(f)\ H_{ant}\ (f)$, where X(f) is the frequency domain representation of x(t). The power of transmitted signal can be calculated using (10).

B. Channel

The primary channel for the communication link is computed from the human tissue layers model. The total losses are computed using (15). For the bit error rate (BER) analysis, one can focus on the wearable-to-sensor channel shown in FIG. 12*b*. By considering the frequency-selective response of the channel, the power of the receiver signal $P_r$ is calculated. The given loss can be translated to the channel transfer function H (f), and after accounting for channel effects signal received $P_r(f)$ can be calculated using the equation:

$$Pr(f) = P_t(f)H(f). \quad (16)$$

Thus, received signal $x_r(t)$ can be calculated by accounting for the frequency-selective channel response.

C. Receiver

At the receiver, to maximize the detection, two matched filters may be used, one for the up-chirp and one for the down-chirp. The impulse response of an ideal matched filter is given by $h(t)=x_r(\tau-t)$, where $x_r(t)$ is the received signal at receiver. For the formulation of BER the noise added to the signal can be accounted for, and this can be represented as $y(t)=x_r(t)+n(t)$, where n(t) is the additive white Gaussian noise. To perform the detection, the received signal is then multiplied with the corresponding up-chirp $s_1(t)$ and down-chirp $s_0(t)$ signal to produce detector outputs.

$$M_i = \sum_{t=0}^{T} y(t)s_i(t)dt, \quad i = 0, 1 \quad 0 \le t \ge T \quad (17)$$

Comparing $M_0$ and $M_1$, the detected bit can be identified. If $M_0>M_1$, the detected bit is "0," and if $M_0<M_1$, the detected bit is "1." The cross-correlation coefficient ρ between up-chirp and down-chirp is defined as:

$$\rho = \frac{1}{\sqrt{E_b}} \sum_{t=0}^{T} s_0(t)s_1(t)dt, \quad (18)$$

where $E_b$ is the energy per bit. For a standard chirp signal probability of error can be analytically expressed as:

$$P_e = \frac{1}{2} erf\left(\frac{E_b}{2N_0}(1-\rho)\right), \quad (19)$$

where $N_0$ is noise power spectral density. The relation between signal to noise ratio (SNR), $E_b$ and $N_0$ is given by:

$$SNR = \frac{R_b}{B}\frac{E_b}{N_0}, \quad (20)$$

where $R_b$ is the bit rate, B is bandwidth, $E_b$ is the energy per bit and $N_0$ is power spectral density of noise.

IX. Numerical Analysis

A. Antenna Chirp Excitation

FIG. 15A is a graph showing a power spectrum of an example linear chirp signal that can be used for antenna excitation in a chirp light source in embodiments. The chirp signal, generated as per (7), spans from 180 THz to 250 THz over a sweep time of 2.5 ns. The power is equally distributed across the entire sweep frequency.

FIG. 15B illustrates the frequency range of "source light" as used herein in different embodiments. In various embodiments, the source light can include frequencies (such as chirp pulses, for example) in at least one of a TeraHertz band of 1-10 THz, a far-infrared (IR) band of 10-180 THz, a mid-IR band of 180-250 THz, a near-IR band of 2560-400 THz, and a visible band of 400-770 THz.

B. Imprinted Chirp Waveform

FIG. 16 is a graph illustrating chirp source light signal power 1606 versus the plasmonic antenna response spectra (emitted light spectral signatures) 1614*a* and 1614*b* for non-binding and binding cases, respectively, of a plasmonic nano-antenna affecting the transmitted signal, having respective peaks 1680*a* and 1680*b* at different frequencies. As illustrated, a chirp pulse in source light can span a range of possible resonant frequencies at the peaks 1680*a* and 1680*b* for the plasmonic nano-antenna.

The chirp in the source light can be up or down in frequency with time. Accordingly, a modulator such as the modulator 134 can be configured to cause the light source to output the source light as chirp-up and chirp-down pulses.

The generated chirp signal is then transmitted through the plasmonic nano-antenna of an embodiment biosensor. To account for the effect of the antenna response on the transmitted chirp, the transfer function of the antenna can be calculated, and the power of the transmitted signal can be calculated using (10). The transmitted signal power is plotted in FIG. 16, as noted above. It can be observed that for binding and non-binding cases, the majority of the power of the transmitted signal is centered around the antenna resonant frequencies.

C. Chirp-Sensing Detection

Figure 17A:
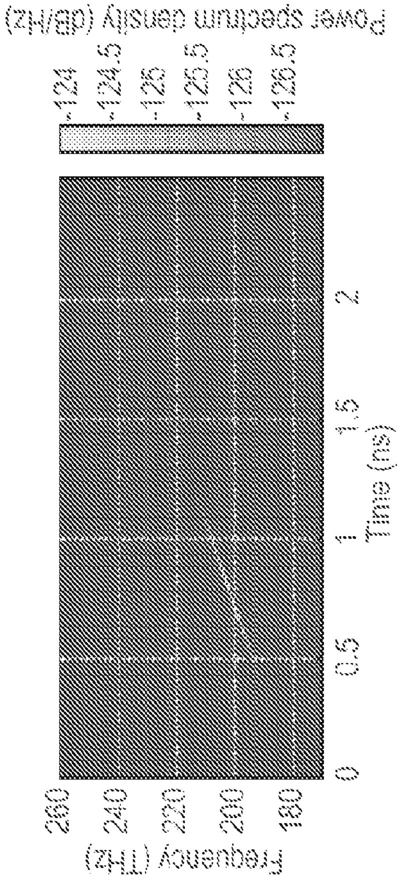
FIGS. 17A-17B are graphs showing detection of antenna resonant frequency before (FIG. 17A) and after (FIG. 17B) biomarker binding using chirp source light.
Figure 17B:
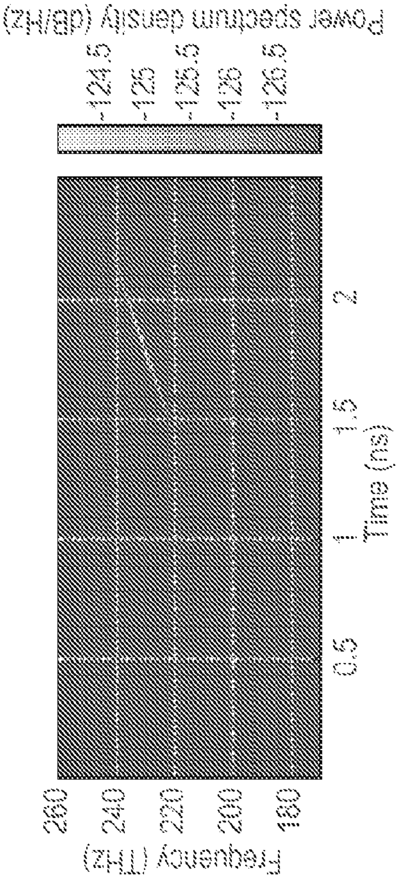

FIGS. 17A-17B are graphs showing detection of antenna resonant frequency before (FIG. 17A) and after (FIG. 17B)

biomarker binding based on the cutoff frequency and power spectrum. This is done by using chirp source light as indicated in FIG. 16.

To perform detection successfully from the received signal, the power is computed and the power spectrum of the received signal is plotted. As shown in FIG. 17*a* for the no biomarker binding case and FIG. 17*b* for the biomarker binding case, the sensing features of binding versus non-binding can be easily distinguished with a peak power cutoff of −127 dB. The example frequency shift from 200 THz to 230 THz demonstrates the use of an antenna with a chirp waveform for successful detection.

D. Joint Communication and Sensing

For joint sensing and communication analysis, the up-chip transmitted signal is modeled as bit 1 and down-chirp as bit 0. Using this symbol encoding, the data packet is encoded and transmitted.

FIGS. 18A-18B are graphs showing a data packet (01001110) transmitted using chirp modulation method with no biomarker binding (FIG. 18A) and with biomarker binding (FIG. 18B). For illustration purposes, as an example, a reference transmitted packet "01001110" with binding is shown in FIG. 18B. It can be observed that most of the power of the packet is transmitted in the antenna binding frequency band ($f_1$). These results for binding detection while up-chirp and down-chirp signals are also clearly distinguishable for successful data packet detection. Similarly, in FIG. 18A, the packet shown is transmitted in the absence of the biomarker and, similarly, the data is easily comprehensible.

In the manner illustrated by FIGS. 18A-18B, the combination of the light source and the plasmonic nano-antenna can be configured to encode the output indicative of the receipt or non-receipt of the biomarker into the optical communication signal, such as by sending a "1" or a "0." Moreover, it will be apparent that any other data desired may be encoded in the same manner, by causing a modulator to effect modulation in the source light, such as the chirp of FIG. 16, resulting in a corresponding modulation being exhibited in the emitted light, as illustrated in FIGS. 17A-17B and 18A-18B. The combination of the light source and the plasmonic nano-antenna can thus be configured to encode an optical communication signal into the emitted light via the corresponding modulation exhibited in the emitted light, corresponding to chirp in the source light.

E. Performance Analysis at Edge

For the performance analysis of this proposed joint communication and sensing system, BER analysis simulation was performed with 10,000 bits. This was compared with the analytical BER of a chirp-based communication system.

Figure 19:
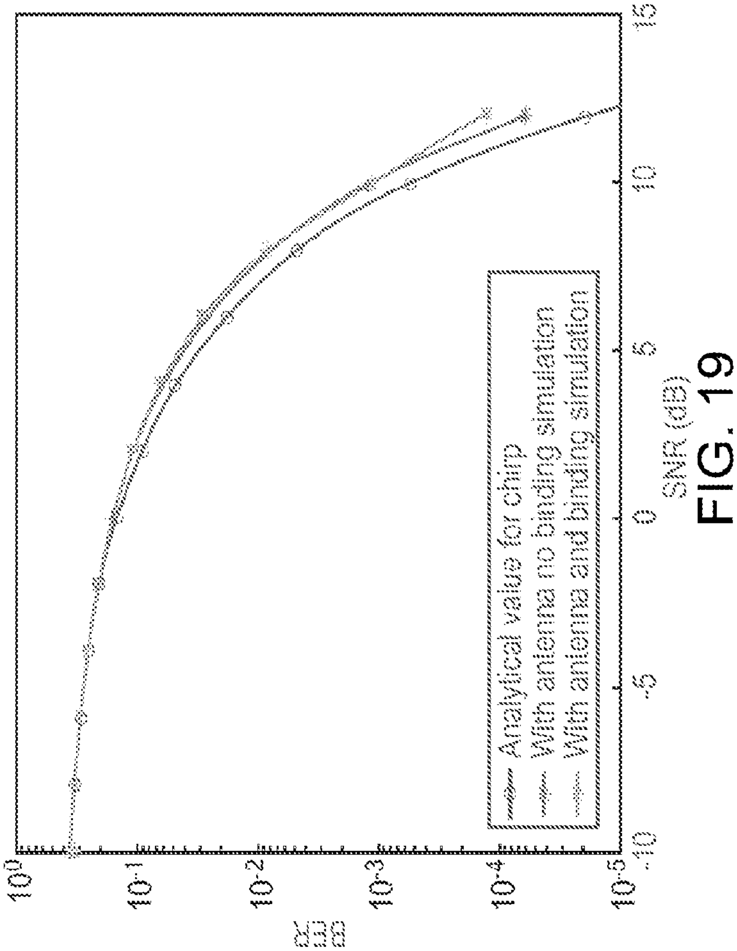
FIG. 19 is a graph illustrating BER analysis of an example embodiment joint communication and sensing waveform with human channel model.

FIG. 19 is a graph illustrating BER analysis of an example embodiment joint communication and sensing waveform with human channel model. FIG. 19 particularly shows the results of simulated analysis of antenna binding and non-binding cases from the sensor to wearable channel and benchmarks them with standard chirp performance for a given SNR. It can be observed that the performance is lower than standard chirp but still closely follows the analytical BER expression of chirp, demonstrating the ability of chirp waveform resilience for communications, even with the imprinted antenna binding features. Such loss of performance can be justified with the antenna's sensing response causing additional losses to the transmitted chirp signal, thus increasing the required SNR to achieve the same BER.

F. Spectrum Bandwidth Optimization

In an embodiment biosensor with communication, there is a trade-off between the efficiency in which the spectral resources are utilized and the complexity of the solution to be implemented by a nanomachine. To tackle this trade-off, different system variations can be made to optimize either the complexity of implementation on a nano-node or the bandwidth occupied by the operational system. Such possible cases for optimization are as follows:

Case 1: Nanomachine complexity minimization. In its current form, the presented arrangement is aimed at reducing the nanomachine complexity while utilizing the entire bandwidth for chirp-based communication. This allows a wide-band receiver with an up-chirp and down-chirp detector to perform signal detection and communication.

Case 2: Spectral efficiency maximization. Given the performance of the antenna as a sensor discussed in Sec. IV, the frequencies of interest are $f_0$ (no binding) and $f_1$ (biomarker binding). To maximize the spectral efficiency, the nanomachine could transmit a narrow band signal first at $f_0$ and then at $f_1$, as part of an initial Request-to-Send (RTS) in the context of a medium access control protocol for nanonetworks. These two signals could be compared by the receiver and followed by a clear to send (CTS) packet selecting the resonant band of the antenna. Therefore, if $Pf_0>Pf_1$, the next packet is sent at $f_0$. Thus, only the resonant antenna band is utilized for transmission to maximize spectral efficiency. The trade-off for such an arrangement is that it requires a 2-way handshake before every data transmission to ensure detection can be reliably made. Such 2-way communication and MAC layer processing will add additional complexity to nano-node architecture. Additionally, if the antenna performs detection between the data packet being sent, it will require initiating a new handshake and might result in the loss of the data packet.

Case 3: Balancing complexity and spectral efficiency. To balance the two previous cases, a solution that can minimize both complexity and bandwidth of operation while resisting the frequency selective channel is needed. Such a unidirectional system can be designed by sending two simultaneous chirps at center frequencies $f_0$ and $f_1$, each with bandwidth $X<(f_1\ f_0)/2$, namely, one chirp centered at $f_0$ (from f0 X/2 to f0+X/2 for the non-binding state and one chirp centered at $f_1$ (from F1 X/2 to f2+X/2) for the binding state. Thus, for any given transmission simultaneous sensing and detection can be performed. The detection results from detector design in the FIG. 13 can be used to select the data detection chirp frequency for minimal addition to the complexity and ease of operation. The required bandwidth X should be calculated using a detailed analysis of factors such as the bio-functional layer used, measured effective shift in antenna resonance with binding, and frequency selective nature of the channel for the band of operation. Therefore, ensuring a balanced and optimized operation of the proposed nano-system.

X. Conclusions

In the manner described above and illustrated in the drawings, an embodiment biosensor that encodes and sends communications signals directly into the sensing light is demonstrated. Through the Internet of Nano-Bio Things architecture, embodiments can bridge nanoscale networks with cloud computing through the edge. The use of a nano patch antenna as a sensor has been investigated by modeling the effects of changing patch thickness and conductivity of the top layer of the antenna on its resonant frequency. It has been demonstrated that a change of resonating frequency can be utilized for simultaneous sensing and communication by using broadband chirp signals and performing a thorough numerical analysis. Further, a detection mechanism can be used for sensing by nanomachines such as biosensors has been demonstrated. A comprehensive analysis has been performed and the communication performance benchmarked to a standard chirp signal. The feasibility of a nano-sensing and communication system that offers the ability to perform edge sensing and can reduce the need for high computational resources required by the conventional spectrometric sensors while maintaining a minimal footprint on a nanomachine node has been established.

ADDITIONAL DETAILS

FIG. 20 is a graph illustrates a meaning of "broadband" as used herein. If a plasmonic nano-antenna has response curve 2006*a* at resonant frequency 2072*a* in a non-binding case without a biomarker present, and response curve 2006*b* at resonant frequency 2072*b* in a binding case with a biomarker present, source light can be "broadband" as used herein if its frequency spectrum 2006*c* spans both of the resonant frequencies. Alternatively, "narrowband" source light, as used herein, would not extend in frequency range from one resonance to another in the same plasmonic nanoantenna. Thus, whether an embodiment light source is narrowband or broadband will be defined in part by the particular frequencies associated with an embodiment plasmonic nano-antenna.

In one alternative detection method, power spectral density in binding and non-binding states may be compared. The source light can include two narrowband frequency components corresponding, respectively, to a first resonant frequency of the plasmonic nano-antenna in a state in which the biomarker is available and a second resonant frequency of the plasmonic nano-antenna in a state in which the biomarker is not available. The two narrowband components can correspond to the peak response frequencies 2072*a* and 2072*b*, for example.

FIG. 21 is a power graph illustrating power differences between a response curve 2112*a* and a response curve 2112*b*, with a narrowband frequency source light spectrum overlapping with a response curve. If the overlapping resonant state is triggered by the appropriate binding state of the bio-functionalized, then the power will be different than if the overlapping resonant state is not triggered. This power difference can be used to detect binding state to determine whether a biomarker is present. Powers of both resonant states may be monitored using two narrowband source light spectra to determine whether the biomarker is present. This is an alternative to chirp pulses for detection in embodiments.

Figure 22:
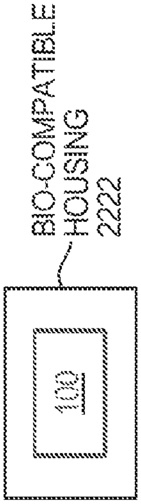
FIG. 22 is a block diagram illustrating an embodiment biosensor optionally encased in biocompatible housing.

FIG. 22 is a block diagram illustrating that the components of an embodiment biosensor 100 may be considered to be "at" the biosensor, as used herein, if the components are optionally encased in the same biocompatible housing 2222. Alternatively, or in addition, the components are considered "at" the biosensor if they are mounted on a common chip forming part of the biosensor or are in close enough proximity to each other to be mounted on a common chip if it formed part of the biosensor.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A biosensor comprising:

a light source at a biosensor, the light source configured to generate modulated source light having a source light spectrum, and the biosensor configured to be implanted into a living being;

a plasmonic nano-antenna at the biosensor, the plasmonic nano-antenna optically coupled to the light source and configured to receive the modulated source light and to emit light exhibiting a spectral signature of the plasmonic nano-antenna; and a bio-functionalized element joined to the plasmonic nano-antenna and configured to receive a biomarker if the biomarker is available, the bio-functionalized element configured to effect a change in the spectral signature as a function of receipt or nonreceipt of the biomarker, wherein a combination of the light source and the plasmonic nano-antenna is configured to encode an optical communication signal into the emitted light by imprinting the spectral signature of the plasmonic nano-antenna onto the modulated source light, and wherein the combination is further configured to transmit the optical communication signal, via the emitted light exhibiting the spectral signature, to a communication node that is physically separated from the biosensor.

2. The biosensor of claim 1, further comprising a detector at the biosensor, the detector configured to detect the emitted light and to provide an output indicative of the receipt or nonreceipt of the biomarker by the bio-functionalized element.

3. The biosensor of claim 2, wherein the combination of the light source and the plasmonic nano-antenna is further configured to encode the output indicative of the receipt or nonreceipt of the biomarker into the optical communication signal.

4. The biosensor of claim 2, wherein the light source, the plasmonic nano-antenna, and the detector are mounted onto a common chip, wherein the plasmonic nano-antenna is further optically coupled to the light source via a light guide on the common chip, and wherein the detector is further configured to receive the emitted light via the light guide.

5. The biosensor of claim 2, wherein the emitted light is reflected from the plasmonic nano-antenna.

6. The biosensor of claim 1, further comprising a modulator configured to effect modulation in the source light, resulting in a corresponding modulation being exhibited in the emitted light, the combination of the light source and the plasmonic nano-antenna being further configured to encode the optical communication signal into the emitted light via the corresponding modulation exhibited in the emitted light.

7. The biosensor of claim 1, wherein source light is broadband, including frequency components spanning a range of possible resonant frequencies of the plasmonic nano-antenna.

8. The biosensor of claim 1, wherein the source light includes two narrowband frequency components corresponding, respectively, to a first resonant frequency of the plasmonic nano-antenna in a state in which the biomarker is available and a second resonant frequency of the plasmonic nano-antenna in a state in which the biomarker is not available.

9. The biosensor of claim 8, the combination of the light source and the plasmonic nano-antenna being further configured to encode the optical communication signal into the emitted light via a power difference between the two narrowband frequency components exhibited in the emitted light.

10. The biosensor of claim 1, wherein the spectral signature of the plasmonic nano-antenna is characterized by a peak or valley in a power spectral density of the emitted light, the peak or valley at a resonant frequency of the plasmonic nano-antenna.

11. The biosensor of claim 10, wherein the change in the spectral signature is a change in frequency or power of the peak or valley in the power spectral density of the emitted light between states of receipt and nonreceipt of the biomarker by the bio-functionalized element.

12. The biosensor of claim 1, wherein the bio-functionalized element comprises a dielectric surface having nanosphere or microsphere particles situated thereon.

13. The biosensor of claim 1, wherein the physically separated communication node is implanted into the living being or wherein the physically separated communication node is wearable on the living being or otherwise external to the living being.

14. The biosensor of claim 1, wherein the light source, the plasmonic nano-antenna, and the bio-functionalized element, are held within a biocompatible housing of the biosensor.

15. The biosensor of claim 1, wherein the light source and the plasmonic nanoantenna are mounted onto a common chip.

16. The biosensor of claim 1, wherein the source light comprises frequencies in a range of 1-770 THz.

17. The biosensor of claim 1, wherein the plasmonic nano-antenna is comprised of a gold or gold alloy layer situated between dielectric layers.

18. The biosensor of claim 1, further comprising a detector at the biosensor, the detector configured to detect the emitted light and to provide an output indicative of the receipt or nonreceipt of the biomarker by the bio-functionalized element, and wherein the detector includes two additional plasmonic nano-antennas with respective resonant frequencies corresponding to resonant frequencies of the plasmonic nano-antenna for receipt and non-receipt of the biomarker, the detector further including a power comparator configured to compare output powers of light emitted from the respective two additional plasmonic nano-antennas.

19. A communication node comprising:

a light source at a first communication node, the light source configured to generate modulated source light having a source light spectrum, and the first communication node configured to be implanted into a living being; and a plasmonic nano-antenna at the first communication node, the plasmonic nano-antenna optically coupled to the light source and configured to receive the modulated source light and to emit light exhibiting a spectral signature of the plasmonic nano-antenna, wherein the first communication node is configured to send an optical communication signal comprising the spectral signature of the plasmonic nano-antenna imprinted onto the modulate source light to a second communication node that is physically separated from the first communication node by using the emitted light exhibiting the spectral signature of the plasmonic nano-antenna.

20. The communication node of claim 19, further comprising a bio-functionalized element joined to the plasmonic nano-antenna and configured to receive a biomarker if the biomarker is available, the bio-functionalized element configured to effect a change in the spectral signature as a function of receipt or nonreceipt of the biomarker.

* * * * *